United States Patent
Kitaoka et al.

(10) Patent No.: US 9,089,644 B2
(45) Date of Patent: Jul. 28, 2015

(54) ADMINISTRATION APPARATUS, OPERATING METHOD THEREOF AND ADMINISTRATION METHOD

(75) Inventors: Yuki Kitaoka, Kyoto (JP); Kenji Kameyama, Kanagawa (JP); Masanobu Nishimiya, Kanagawa (JP)

(73) Assignees: RICOH COMPANY, LTD., Tokyo (JP); Yuki Kitaoka, Kyoto (JP)

( * ) Notice: Subject to any disclaimer, the term of this patent is extended or adjusted under 35 U.S.C. 154(b) by 36 days.

(21) Appl. No.: 13/822,054

(22) PCT Filed: Sep. 8, 2011

(86) PCT No.: PCT/JP2011/071058
§ 371 (c)(1),
(2), (4) Date: Mar. 11, 2013

(87) PCT Pub. No.: WO2012/036226
PCT Pub. Date: Mar. 22, 2012

(65) Prior Publication Data
US 2013/0165906 A1    Jun. 27, 2013

(30) Foreign Application Priority Data
Sep. 14, 2010   (JP) ................................. 2010-205881

(51) Int. Cl.
*A61M 5/172* (2006.01)
*A61M 5/14* (2006.01)
*G06F 19/00* (2011.01)

(52) U.S. Cl.
CPC .................. *A61M 5/172* (2013.01); *A61M 5/14* (2013.01); *G06F 19/3456* (2013.01)

(58) Field of Classification Search
CPC ............... A61M 5/14244; A61M 2005/14208; A61M 5/14; A61M 5/142; A61M 31/002; G06F 19/3456

USPC .................................. 604/506, 500, 890.1
See application file for complete search history.

(56) References Cited

U.S. PATENT DOCUMENTS 4,299,541 A   11/1981   Ohara et al.
7,872,048 B2  1/2011    Simard (Continued)

FOREIGN PATENT DOCUMENTS

JP   11-019210    1/1999
JP   2004-026811  1/2004

(Continued)

OTHER PUBLICATIONS

Altinok, et al. A cell cycle automaton model for probing circadian patterns of anticancer drug delivery. Jun. 28, 2007. Advanced Drug Delivery Reviews, 59, pp. 1036-1053.*
Russian Office Action dated Jul. 8, 2014.
Second Dug Subcommittee, Pharmaceutical Affairs and Food Sanitation Council, "Anticancer Drug Report: Fluorouracil and Isovorin (Colorectal Cancer)", Aug. 27, 2004 (with English Translation).

(Continued)

*Primary Examiner* — Nicholas Lucchesi
*Assistant Examiner* — Weng Lee
(74) *Attorney, Agent, or Firm* — IPUSA, PLLC

(57) ABSTRACT

An administration apparatus to administer an inhibitor drug to a patient to inhibit cell division of a malignant cell includes an administration unit configured to administer the inhibitor drug to the patient; an administration timing storage unit configured to store an administration time to start an administration of the inhibitor drug; a time measurement unit configured to measure a current time; and a control unit configured to drive and control the administration unit so as to administer the inhibitor drug to the patient when the current time coincides with the administration time. The administration time is set on a basis of a predetermined phase of a cell cycle of the malignant cell.

14 Claims, 15 Drawing Sheets

(56) References Cited

U.S. PATENT DOCUMENTS

| | | | |
|---|---|---|---|
| 2002/0095258 A1* | 7/2002 | Agur et al. | 702/19 |
| 2003/0129262 A1* | 7/2003 | Epner et al. | 424/757 |
| 2003/0144798 A1* | 7/2003 | Gardner | 702/19 |
| 2004/0077997 A1 | 4/2004 | Jasperson et al. | |
| 2005/0165384 A1 | 7/2005 | Gravesen et al. | |
| 2005/0277911 A1 | 12/2005 | Stewart et al. | |
| 2006/0199189 A1* | 9/2006 | Bradford | 435/6 |
| 2006/0271020 A1* | 11/2006 | Huang et al. | 604/890.1 |
| 2007/0003964 A1 | 1/2007 | Matsushima et al. | |
| 2007/0185150 A1 | 8/2007 | Bedrosian | |
| 2007/0248589 A1* | 10/2007 | Flomerfelt et al. | 424/130.1 |
| 2009/0177147 A1 | 7/2009 | Blomquist et al. | |
| 2009/0203636 A1* | 8/2009 | Bondarev | 514/45 |
| 2011/0159111 A1 | 6/2011 | Curry et al. | |

FOREIGN PATENT DOCUMENTS

| | | |
|---|---|---|
| JP | 2007-037540 | 2/2007 |
| JP | 2008-513447 | 5/2008 |
| JP | 2009-515901 | 4/2009 |
| JP | 2009-542608 | 12/2009 |
| RU | 2279898 | 7/2006 |
| WO | 2010/053703 | 5/2010 |
| WO | 2010/054314 | 5/2010 |

OTHER PUBLICATIONS

Nippon Kayaku Co., Ltd., "Oncovin for Injection 1mg", Revised Fifth Edition, Aug. 2009 (with English Translation).

International Search Report Issued Nov. 1, 2011 in PCT/JP2011/071058 Filed on Sep. 8, 2011.

Cojocaru et al., "A theoretical analysis of interval drug dosing for cell-cycle-phase-specific drugs", Mathematical Biosciences 109:85-97 (1992).

Gardner S. N., "A mechanistic, predictive model of dose-response curves for cell cycle phase-specific and -nonspecific drugs", Cancer Res. Mar. 1, 2000; 60(5):1417-25.

Altinok A. et al., "A cell cycle automaton model for probing circadian patterns of anticancer drug delivery", Adv Drug Deliv Rev. Aug. 31, 2007;59(9-10):1036-53. Epub Jun. 28, 2007.

Australian Patent Examination Report No. 2 dated Feb. 20, 2014.

Extended European Search Report dated Mar. 18, 2015.

B. F. Dibrov et al: "Mathematical Model of Cancer Chemotherapy. Periodic Schedules of Phase-Specific Cytotoxic-Agent Administration Increasing the Selectivty of Therapy." May 15, 1984, pp. 1-31, Elsevier Science Publishing Co., Inc., 1985, New York.

George W. Swan: "Review Role of Optimal Control Theory in Cancer Chemotherapy", Apr. 10, 1990, pp. 237-284, Elsevier Science Publishing Co., Inc., 1990, New York.

Japanese Office Action dated Sep. 9, 2014.

* cited by examiner

FIG.1

| NAME OF DRUG | DOSING STRATEGY |
|---|---|
| METHOTREXATE | INFANT 1.25-2.5 MILLIGRAM<br>CHILD 2.5-5 MILLIGRAM<br>ADULT 5-10 MILLIGRAM PER DAY, INJECTED THREE TO SIX TIMES PER WEEK.<br>INTRASTHECALLY INJECTED EVERY TWO TO SEVEN DAYS IN INJECTION DOSE OF 0.2-0.4 MILLIGRAM PER KILOGRAM OF BODY WEIGHT FOR PERIOSTEUM SYMPTOMS (PERIOSTEUM LEUKEMIA) BY MENINGEAL INFILTRATION OF LEUKEMIA. |
| | TROPHOBLASTIC DISEASE<br>USUALLY INJECTED 10-30 MILLIGRAM PER DAY FOR ADULT AS METHOTREXATE MAKING FIVE DAYS A COURSE. DRUG HOLIDAYS USUALLY SEVEN TO TWELVE DAYS, BUT EXPANDED UNTIL SIDE EFFECT DISAPPEARS IF THE SIDE EFFECT OCCURS BY PREVIOUS INJECTION. |
| EFFECTIVENESS | SARCOMA: MORE THAN EFFECTIVENESS OF PULMONARY METASTASIS 20%<br>ACUTE LEUKEMIA: EFFECTIVENESS 70% IF INEFFECTIVE TO OTHER DRUGS AND CENTRAL NERVOUS SYSTEM MOIST<br>MALIGNANT LYMPHOMA: EFFICACY RATE 17% FOR SIX CASES OF MALIGNANT LYMPHOMA INEFFECTIVE TO OTHER DRUGS AND CENTRAL NERVOUS SYSTEM MOIST<br>STOMACH CANCER: EFFICACY RATE 40.5% FOR 37 CASES |

FIG.2

| NAME OF DRUG | DOSING STRATEGY |
|---|---|
| 5-FLUOROURACIL | A METHOD:<br>• LEVOFOLINATE 100 MILLIGRAM / SQUARE METER EVERY TIME (DRIP INJECTION FOR TWO HOURS)<br>• INTRAVENOUS PUSH OF FLUOROURACIL 400 MILLIGRAM / SQUARE METER JUST AFTER FINISHED<br>• MOREOVER, DRIP INJECTION FOR 22 HOURS OF FLUOROURACIL 400 MILLIGRAM / SQUARE METER<br>ABOVE ADMINISTRATION CONTINUOUSLY PERFORMED FOR TWO DAYS<br>• REPEATED EVERY TWO WEEKS<br><br>B METHOD:<br>• LEVOFOLINATE 250 MILLIGRAM / SQUARE METER EVERY TIME (DRIP INJECTION FOR TWO HOURS)<br>• 24-HOUR CONTINUOUS INTRAVENOUS PUSH OF FLUOROURACIL 2600 MILLIGRAM / SQUARE METER JUST AFTER FINISHED<br>ABOVE ADMINISTRATION REPEATED SIX TIMES PER WEEK. DRUG HOLIDAYS FOR TWO WEEKS AFTER THAT<br>ABOVE ADMINISTRATION MADE A COURSE<br><br>C METHOD:<br>• LEVOFOLINATE 200 MILLIGRAM / SQUARE METER EVERY TIME (DRIP INJECTION FOR TWO HOURS)<br>• INTRAVENOUS PUSH OF FLUOROURACIL 400 MILLIGRAM / SQUARE METER JUST AFTER FINISHED<br>• MOREOVER, 46-HOUR DRIP INJECTION OF FLUOROURACIL 2400-3000 MILLIGRAM / SQUARE METER<br>• REPEATED EVERY TWO WEEKS |

FIG.3

| TREATMENT | TEST TYPE | NUMBER OF CASES | RESPONSE RATE(%) | CR/PR(%) | SURVIVAL PERIOD MEDIAN SURVIVAL (MONTH) |
|---|---|---|---|---|---|
| Mayo | PHASE III | 216<br>167 | 14<br>12 | 2/12<br>0/12 | 14.2<br>11.9 |
| De Gramont | PHASE III | 217 | 32.6 | 6/27 | 15.5 |
| AIO | PHASE III | 164 | 17 | 2/15 | 13.7 |
| Roswell Park (JAPAN) | PHASE II | 70 | 30 | 0/30 | 9.9 |

FIG.4

| NAME OF DRUG | DOSING STRATEGY |
|---|---|
| VINCRISTINE | 1. INJECTED INTRAVENOUSLY ONCE A WEEK 0.05-0.1 MILLIGRAM / KILOGRAM FOR CHILD, 0.02-0.05 MILLIGRAM / KILOGRAM FOR ADULT HOWEVER, SINGLE DOSE LESS THAN TWO MILLIGRAM TO AVOID SIDE EFFECT |
| | 2. IF COMBINATION TREATMENT WITH OTHER ANTINEOPLASTIC DRUG AGAINST MULTIPLE MYELOMA IS PERFORMED, STANDARD DOSAGE AMOUNT AND ADMINISTRATION METHOD OF VINCRISTINE IS 24-HOUR CONTINUOUS INTRAVENOUS INJECTION OF 0.4 MILLIGRAM PER DAY IN COMBINATION USE WITH DOXORUBICIN HYDROCHLORIDE, DEXAMETHASONE SODIUM PHOSPHATE. AFTER THAT, HOLIDAY DRUG FOR 17-24 DAYS IS TAKEN. ABOVE IS MADE A COURSE, AND ADMINISTRATION IS REPEATED. |
| | 3. IF COMBINATION TREATMENT WITH OTHER ANTINEOPLASTIC DRUG AGAINST GLIOMA INCLUDING MALIGNANT ASTROCYTOMA MULTIPLE AND OLIGODENDROGLIOMA COMPONENT MYELOMA IS PERFORMED, INTRAVENOUS INJECTION OF 1.4 MILLIGRAM / SQUARE METER IS PERFORMED TWO TIMES AS VINCRISTINE SULFATE. SECOND ADMINISTRATION IS PERFORMED AFTER THREE WEEKS OF FIRST ADMINISTRATION, AND ADMINISTRATIONS ARE REPEATED, MAKING SIX TO EIGHT WEEKS A COURSE. HOWEVER, SINGLE DOSE IS LESS THAN TWO MILLIGRAM TO AVOID SIDE EFFECT. |

FIG.5

| DISEASE NAME | NUMBER OF CLINICAL CASES | NUMBER OF REMISSION CASES | REMISSION RATE (%) |
|---|---|---|---|
| LEUKEMIA: ACUTE LEUKEMIA (CHILD) | 42 | 26 | 61.9 |
| LEUKEMIA: ACUTE LEUKEMIA (ADULT) | 47 | 17 | 36.2 |
| LEUKEMIA: ACUTE LEUKEMIA (SUBTOTAL) | 89 | 43 | 48.3 |
| LEUKEMIA: CHRONIC LEUKEMIA (BLAST CRISIS) | 3 | 2 | 66.7 |
| MALIGNANT LYMPHOMA: RETICULOSARCOMA | 21 | 15 | 71.4 |
| MALIGNANT LYMPHOMA: LYMPHOSARCOMA | 16 | 10 | 62.5 |
| MALIGNANT LYMPHOMA: HODGKIN'S DISEASE | 19 | 16 | 84.2 |
| MALIGNANT LYMPHOMA: SUBTOTAL | 56 | 41 | 73.2 |
| CHILDHOOD TUMOR: NEUROBLASTOMA | 12 | 8 | 66.7 |
| CHILDHOOD TUMOR: WILMS' TUMOR | 2 | 2 | |
| CHILDHOOD TUMOR: EMBRYONAL TESTICULAR CANCER | 2 | 2 | |
| CHILDHOOD TUMOR: RHABDOMYOSARCOMA | 2 | 1 | |
| CHILDHOOD TUMOR: ANGIOSARCOMA | 1 | 1 | |
| CHILDHOOD TUMOR: OSTEOSARCOMA | 1 | 0 | |
| CHILDHOOD TUMOR: RETINOBLASTOMA | 1 | 0 | |
| CHILDHOOD TUMOR: LIPOSARCOMA | 1 | 0 | |
| CHILDHOOD TUMOR: ADRENAL CORTEX CANCER | 1 | 0 | |
| CHILDHOOD TUMOR: SUBTOTAL | 23 | 14 | 60.9 |

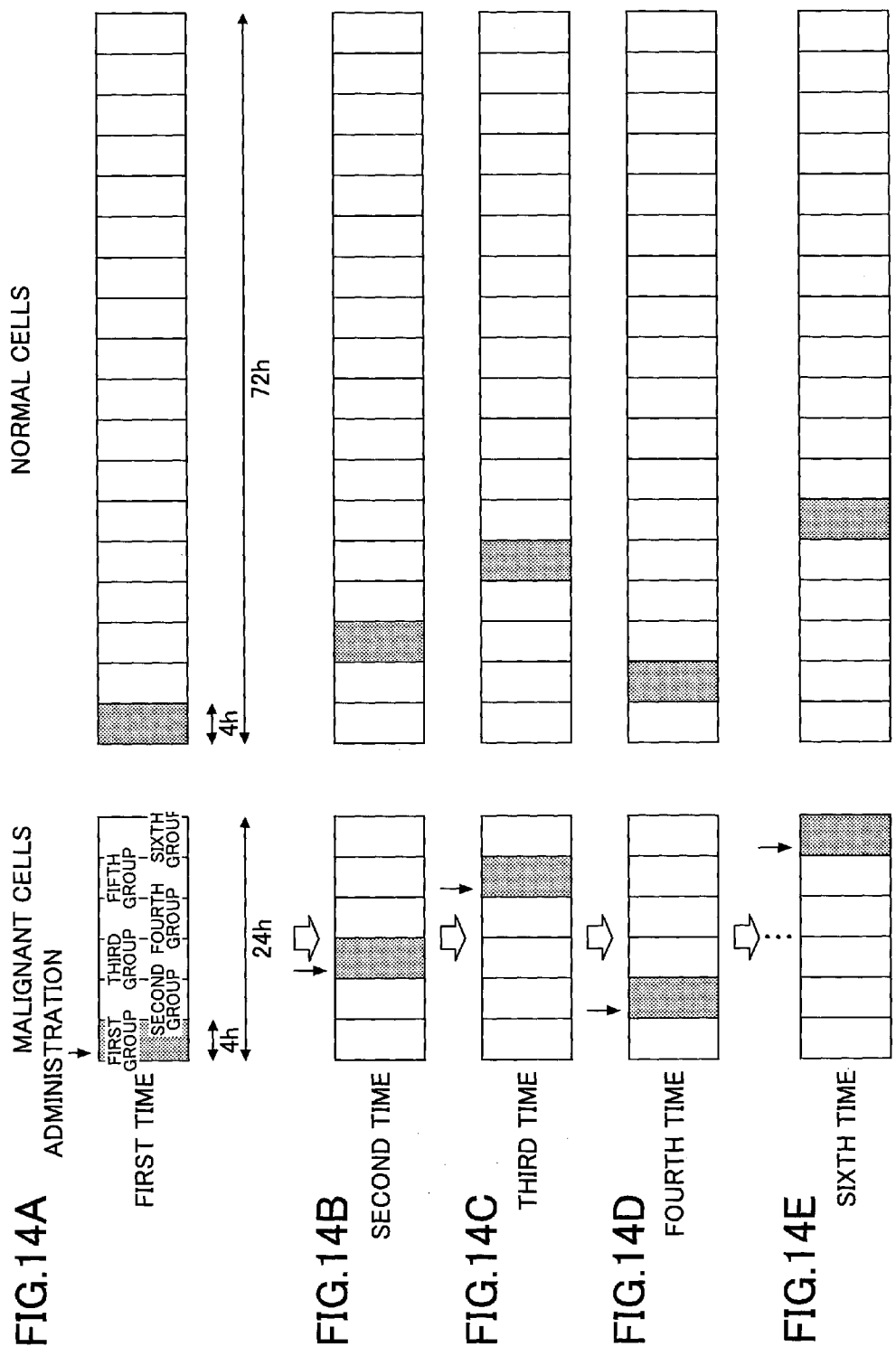

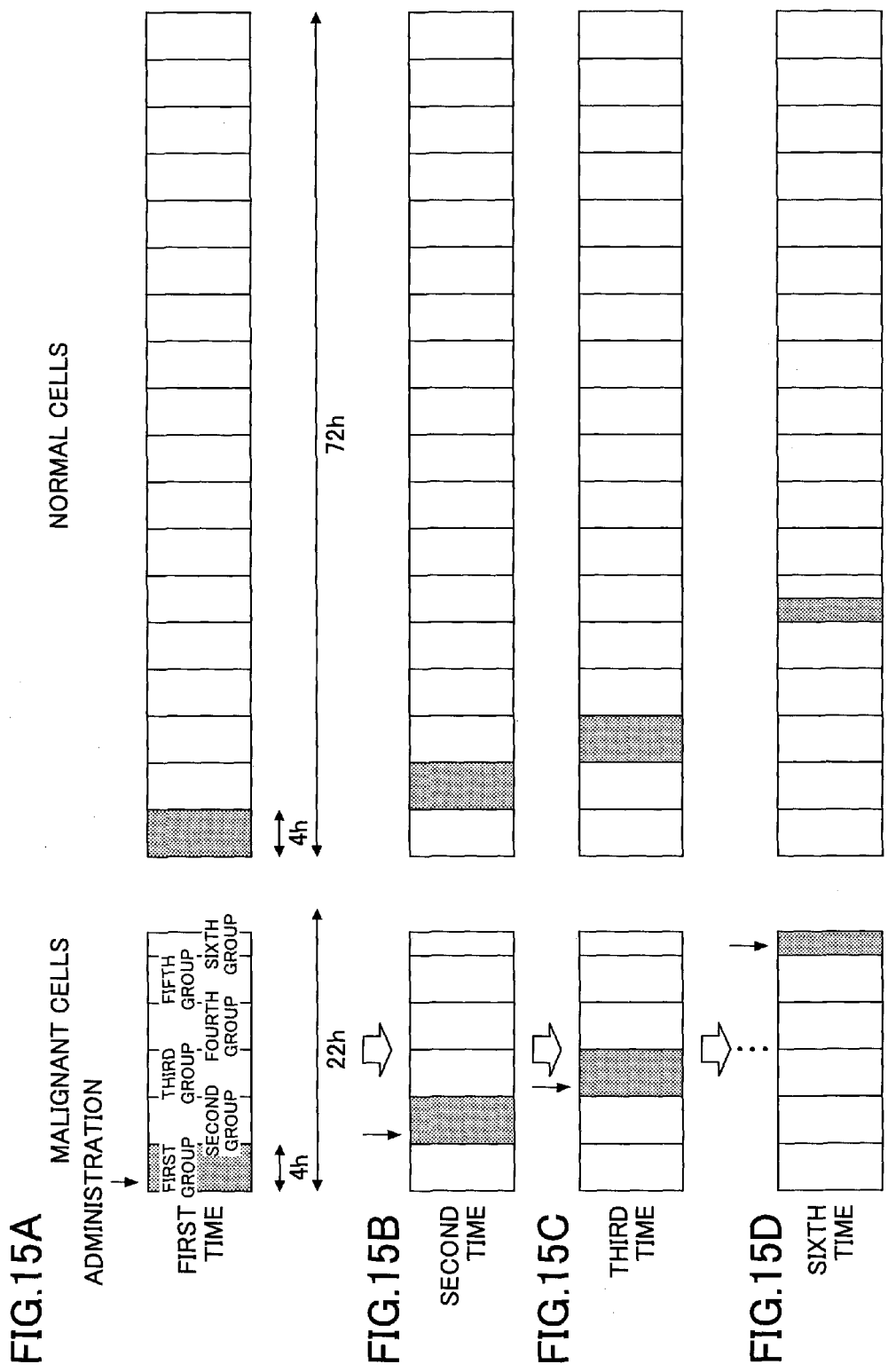

ADMINISTRATION APPARATUS, OPERATING METHOD THEREOF AND ADMINISTRATION METHOD

TECHNICAL FIELD

The present invention generally relates to administration apparatuses, operating methods thereof and administration methods. More specifically, the present invention relates to an administration apparatus, an operating method thereof and an administration method to administer an inhibitor drug that inhibits cell division of a malignant cell to a patient.

BACKGROUND ART

FIGS. 1 through 5 show conventional typical administration methods and efficacy rates of anticancer drugs. FIG. 1 is a table showing conventional administration methods and efficacy rates of methotrexate. FIG. 2 is a table showing conventional administration methods 5-fluorouracil. FIG. 3 is a table showing a randomized trial result of various treatments that have been conventionally practiced in Japan, Europe and the United States. FIG. 4 is a table showing conventional administration methods of vincristine. FIG. 5 is a table showing remission rates for various malignant tumors in conventional administration methods.

All administration methods shown in FIGS. 1 through 5 are methods that perform injections or drip injections, take drug holidays for weeks until a side effect of administrations disappears, and repeat the administrations (see, for example, Non-patent Document 1 and Non-patent Document 2).

However, the conventional administration methods shown in FIGS. 1 through 5 have had a problem of anticancer drugs not being able to exert their effectiveness sufficiently because drug solutions are administrated at arbitrary timing without respect to a cell cycle of a cancer cell. This regard is discussed in detail below with reference to accompanying drawings.

FIG. 6 is a diagram showing an example of a cell cycle. The cell cycle is a concept of viewing a process where the cells divide and the number of cells doubles as a single cycle. The cell cycle is formed of a cycle composed of respective phases including a DNA synthesis preparation phase (i.e., nymphochrysalis: G1 phase), a DNA synthesis phase (S phase), a cell division preparation phase (imagochrysalis: G2 phase), and a cell division phase (M phase). Here, cells that temporarily or reversibly stop the cell division are regarded to be in a stationary phase called G0 phase. A single cancer cell doubles by completing the cell cycle, and continues to doubly increase. The anticancer drug is a generic name of a medical drug, agent or substance that has a function of inhibiting proliferation of the cancer cells, and is roughly divided into two kinds, a time-dependent type drug and a concentration-dependent type drug. The time-dependent type drug shows its effectiveness related to the cell cycle.

It is thought that the time-dependent type anticancer drug effectively acts on G1 phase of the cell cycle shown in FIG. 6, and shows the effectiveness by putting a brake on the progress. The cancer is composed of many cancer cells, and the respective cancer cells are in different phases of the cell cycle. Therefore, even if the anticancer drug is administered in certain timing, the effectiveness of the anticancer drug can be obtained only to the cancer cells in G1 phase at the administered timing, and the anticancer drug cannot produce the effect on the cells in the other phases.

Here, if the cell cycle of the cancer cells is made T, and a period of G1 phase where the anticancer drug can produce the effect is made t, when the anticancer drug at first is administered in a certain timing, a ratio of the number of cells that the anticancer drug can prevent the cell division is t/T to all cells, and a rate of the number of cells that escape from the effect is (T−t)/T to all cells. If the conventional administration methods are repeated n times (where n is an integer), a ratio of the number of cells that escape from the effect after n times is $((T-t)/T)^n$.

As an example, if the cell cycle T is made 24 h; G1 phase t is made 4 h; and the number of administration is made six times, it is found that $(20/24)^6=0.3349=33.5\%$ of the cancer cells remain.

That means that the conventional administration methods have a problem of not being able to exclude the cancer cells that escape from the inhibitory effect in theory, even if the frequency of administration is increased.

Furthermore, because a continuous administration time is long, there is a problem of a physical and mental strain of a patient who receives a dose being great. More specifically, since a small amount of anticancer drug is diluted with a solution, and a treatment is carried out by giving the patient a drip continuously for a long time, the patient comes to take large volumes of fluid. Because of this, the patient has to go to a restroom frequently, which causes a large burden to the patient. Moreover, because the conventional administration methods impose on the kidneys of the patient, there has been a problem of not being able to perform the administration to the patient having a kidney disorder. In addition, if the administration is performed by hospital visit, the best timing can be midnight, depending on the administration timing. In this case, there has been a problem of the administration being a burden for both of a healthcare professional and the patient.

[Non-patent Document 1] "Anticancer Report: Fluorouracil and Leucovorin (Colorectal cancer)", online, Aug. 11, 2010 searched, Internet, <URL:http://www.mhlw.go.jp/shingi/2004/05/dl/s0521-5o.pdf>

[Non-patent Document 2] "Oncovin", online, Aug. 11, 2010 searched, Internet <URL: http://www.info.pmda.go.jp/go/pack/4240400D1030_2_06/>

DISCLOSURE OF INVENTION

Accordingly, embodiments of the present invention may provide an administration apparatus, an operating method thereof and an administration method solving one or more of the problems discussed above.

More specifically, the embodiments of the present invention may provide an administration apparatus to administer an inhibitor drug to a patient to inhibit cell division of a malignant cell including:

an administration unit configured to administer the inhibitor drug to the patient;

an administration timing storage unit configured to store an administration time to start an administration of the inhibitor drug;

a time measurement unit configured to measure a current time; and a control unit configured to drive and control the administration unit so as to administer the inhibitor drug to the patient when the current time coincides with the administration time, wherein the administration time is set on a basis of a predetermined phase of a cell cycle of the malignant cell.

According to another aspect of the present invention, an operating method of an administration apparatus, the administration apparatus including, an administration unit configured to administer an inhibitor drug to a patient to inhibit cell division of a malignant cell;

an administration timing storage unit configured to store an administration time to start an administration of the inhibitor drug;

a time measurement unit configured to measure a current time;

an administration period storage unit to store an administration period of administering the inhibitor drug continuously to the patient; and a control unit configured to drive and control the administration unit so as to administer the inhibitor drug to the patient when the current time coincides with the administration time, the operating method including the steps of:

setting the administration time and the administration period on a basis of a predetermined phase of the cell division of the malignant cell;

storing the set administration time in the administration time storage unit and the set administration period in the administration period storage unit respectively; and administering the inhibitor drug to the patient continuously for the administration period when the current time measured by the time measurement unit coincides with the administration time by controlling the administration unit with the control unit.

According to another aspect of the present invention, an administration method to administer an inhibitor drug to a patient to inhibit cell division of a malignant cell, including the steps of:

setting an administration time to start an administration of the inhibitor drug to the patient on a basis of a predetermined phase of the cell division of the malignant cell;

storing the set administration time in an administration time storage unit; and administering the inhibitor drug to the patient continuously when the current time coincides with the administration time stored in the administration storage unit.

BRIEF DESCRIPTION OF THE DRAWINGS

FIG. 1 is a table showing conventional administration methods and efficacy rates of methotrexate;

FIG. 2 is a table showing conventional administration methods for 5-fluorouracil;

FIG. 3 is a table showing a randomized trial result of various treatments that have been conventionally practiced in Japan, Europe and the United States;

FIG. 4 is a table showing conventional administration methods of vincristine;

FIG. 5 is a table showing remission rates for various malignant tumors in conventional administration methods;

FIG. 14A is a diagram showing an example of a first administration of an operating method of an administration apparatus and an administration method of a fourth embodiment;

FIG. 14B is a diagram showing an example of a second administration of the operating method of the administration apparatus and the administration method of the fourth embodiment;

FIG. 14C is a diagram showing an example of a third administration of the administration method of the fourth embodiment;

FIG. 14D is a diagram showing an example of a fourth administration of the operating method of the administration apparatus and the administration method of the fourth embodiment;

FIG. 14E is a diagram showing an example of a sixth administration of the operating method of the administration apparatus and the administration method of the fourth embodiment;

FIG. 15A is a diagram showing an example of a first administration of an operating method of an administration apparatus and an administration method of a fifth embodiment;

FIG. 15B is a diagram showing an example of a second administration of the operating method of the administration apparatus and the administration method of the fifth embodiment;

FIG. 15C is a diagram showing an example of a third administration of the operating method of the administration apparatus and the administration method of the fifth embodiment; and FIG. 15D is a diagram showing an example of a sixth administration of the operating method of the administration apparatus and the administration method of the fifth embodiment.

DESCRIPTION OF EMBODIMENTS

A description is given below, with reference to accompanying drawings of embodiments of the present invention.

Figure 6:
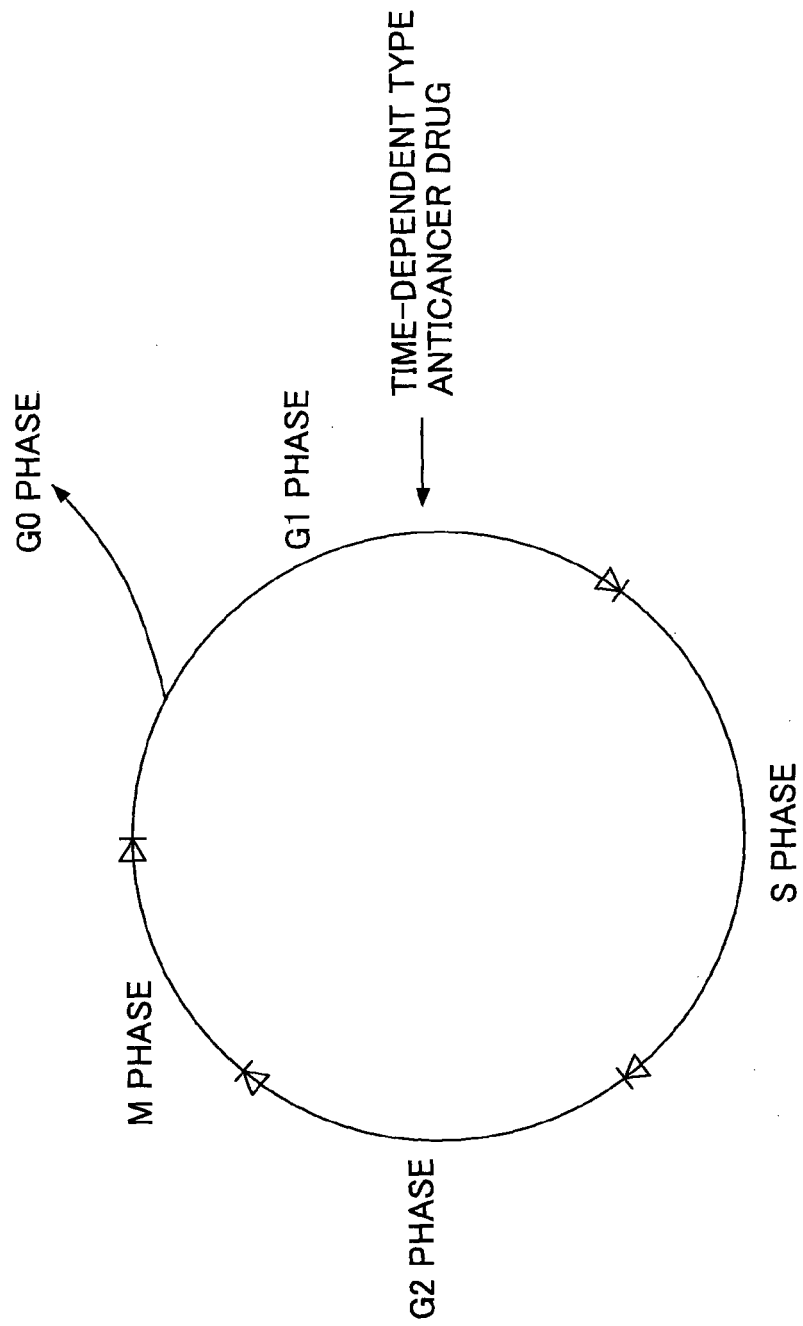
FIG. 6 is a diagram showing an example of a cell cycle.

FIG. 6 is a diagram showing an example of a cell cycle. As mentioned above, the cell cycle is a concept of viewing a process where cells divide and the number of cells doubles as a single cycle. The cell cycle is formed of a cycle composed of respective phases of a DNA synthesis preparation phase (i.e., nymphochrysalis: G1 phase), a DNA synthesis phase (S phase), a cell division preparation phase (imagochrysalis: G2 phase), and a cell division phase (M phase). A cancer cell becomes two cancer cells by going round the cell cycle once, the number of the cells continues to double. An anticancer drug is a generic name of a medical drug, agent or substance that has a function of inhibiting proliferation of the cancer cells, and roughly divided into two kinds of drugs, a time-dependent type drug and a concentration-dependent type drug. The time-dependent type drug shows its effect related to the cell cycle. A phase that shows the effect of inhibiting proliferation of the cancer cell is made a predetermined phase.

It is thought that the time-dependent type anticancer drug acts effectively on the G1 phase of the cell cycle shown in FIG. 6, and shows its effect by putting a brake on the progress. Because the cancer is composed of many cancer cells, and respective caner cells are in different phases in the cell cycle, the anticancer drug that works on the G1 phase shows a more highly effect by a long time administration. As typical time-dependent type anticancer drugs, 5-fluorouracil, methotrexate, vincristine and the like are cited as examples.

Here, a concentration-dependent type drug has a character that increases cell killing effectiveness as a dosage amount increases (concentration dependency), and massive dose is performed just the same.

On the other hand, the anticancer drug has a function that inhibits the cell division, or harms the cells directly, and naturally causes damage even to normal cells. More specifically, the anticancer drug may cause damage to a bone marrow where cell proliferation is active (where a blood cell is created), an alimentary canal mucosa, and a liver or a kidney that has functions of decomposing a drug and carrying the drug out of the body. The more the anticancer drug is used, the more a side effect is caused. Therefore, it is necessary to use the anticancer drug, considering a balance between the effect and the side effect of the anticancer drug.

In the cell cycle shown in FIG. 6, if the anticancer drug effectively acts on the G1 phase, by administering the anticancer drug to each cancer cell only in the G1 phase, the anticancer drug can be administered most effectively, and the side effect on the normal cells can be reduced.

However, in reality, the plural cancer cells exist in the patient's body, and the respective cancer cells advance the respective cell cycles in different timings. Accordingly, all of the cancer cells do not enter the G1 phase together in the same timing, but the respective cancer cells enter the G1 phase in different timings. Because of this, in the conventional anticancer drug administration methods, there have been no other methods than administering the anticancer drug in an arbitrary timing by ignoring the cell cycle, or administering the anticancer drug diluted to a low concentration into the patient's body for a long time. Due to this, the anticancer drug has not been able to produce the cell division inhibition effect sufficiently, and the burden on the patient and the healthcare professional has been great in the event of the long time continuous administration.

First Embodiment

FIGS. 7A through 7D are diagrams to illustrate a basic principle of an administration method of a first embodiment. FIG. 7A is a diagram showing an example of a first administration of an administration method of a first embodiment in comparison to an effect to normal cells. Similarly, FIG. 7B shows a second administration of the administration method of the first embodiment; FIG. 7C is shows a third administration of the administration method of the first embodiment; and FIG. 7D shows a sixth administration of the administration method of the first embodiment in comparison to the effect to normal cells respectively.

In FIGS. 7A through 7D, as an example, a cell cycle of cancer cells is made 24 hours (24 h), and a time length (or a time period) of G1 phase where an anticancer drug functions is made four hours (4 h). Also, a cell cycle of normal cells is made 72 hours (72 h).

In this case, as shown in FIG. 7A, if the time length of the G1 phase (4 h) is made a standard, and the cell cycle (24 h) is divided by the time length of the G1 phase as a basic unit, the cell cycle can be divided into 24/4=6 groups. All of the cancer cells enter the G1 phase at any timing in the six groups. Here, the G1 phase of the respective cancer cells do not always start and finish at the same timings as the six groups' start and end, but spread over two groups in many cases, which has no problem, though. This point is described hereinafter.

At the first administration timing, the cells in a period when the anticancer drug works exist in a 4/24=1/6 probability. If this is called a first group, the anticancer drug works on the cancer cell in the first group. In the first anticancer drug administration, the anticancer drug is continuously administered for a predetermined period in four hours of the time length of the G1 phase, and the administration is stopped. The administration period varies according to the anticancer drug. For example, the administration period may be a several minutes or may be a few hours within four hours.

As shown in FIG. 7B, after the first administration, the administration is stopped, and a second administration is performed. At this time, if the second administration timing is made 24 hours after the start of the first administration, which is the same as the cycle time, because the anticancer drug is administered only to the cancer cell in the first group, and have the effect of the cancer inhibition only on the cancer cells in the first group, there is only a small inhibition effect on the whole cancer cells. Accordingly, the second administration is, for example, performed 28 hours after the start of the first administration, by which the administration timing is adjusted so as to take effect on the cancer cells in the second group. By doing this, the anticancer drug can exert the effect on the cancer cells in both of the first and second groups. At this time, the anticancer drug is administered to the cancer cells that enter the G1 phase at timing that spreads over the first group and the second group so as to cover the entire G1 phase, and the anticancer drug can be administered to the cancer cells uniformly.

Next, as shown in FIG. 7C, in a third administration, the anticancer drug is administered so that the anticancer drug exerts effectively on the cancer cells in the third group. That means that the administration is performed 28 hours after the second administration. In addition, the administration period may be the same as the period of the first time and the second time, or may be different from the period of the first time and the second time according to a property and the like of the anticancer drug.

Though not shown in FIGS. 7A through 7D, by repeating fourth and fifth administrations every 28 hours for 4 hours period intermittently in a way similar to the second and third times, the anticancer drug can be administered to the cancer cells that enter the G1 phase in the fourth and fifth groups so that the anticancer drug can effectively work on the cancer cells in the fourth and fifth groups.

As shown in FIG. 7D, if the sixth administration is performed another 28 hours after the fifth administration, the cell division inhibition effect of the anticancer drug can be provided for the all cancer cells. Though the anticancer drug also affects the normal cells, as shown in the right side of FIGS. 7A through 7D, because a cell cycle of the normal cells is 72 hours, a single administration affects only 4/72=1/18 of the all normal cells, and even the all six-time administrations affect only 24/72=1/3 of the all normal cells.

In this way, by dividing a cell cycle into plural groups on a basis of a predetermined time (or a predetermined period) where an anticancer drug can act effectively on cancer cells, by intermittently administering the anticancer drug to the divided plural groups on the basis of the predetermined time in sequence, by finally administering the anticancer drug to all the groups, and by providing the anticancer drug for the entire cell cycle, the anticancer drug can be administered effectively to the cancer cells, reducing an adverse effect on the normal cells.

Here, in the present embodiment, the cell cycle of the malignant cells are divided by using the continuous period of the G1 phase where the anticancer drug inhibits the proliferation of the malignant cells as a basic unit, but it is possible to make the basic unit for division a shorter period than that of the G1 phase. Even in this case, by intermittent and comprehensive administrations, the anticancer drug can be administered to all the malignant cells at the G1 phase timing, reducing the effect on the normal cells.

However, if the divided period is shorter than the G1 phase, fear of performing an overlapping administration to the same malignant cells increases. In other words, when the administration period is quite short, and the administration is viewed as a point in terms of time, as the example described in FIGS. 7A through 7D, if the basic unit for division is the same as the G1 phase, the malignant cells' reception of the administration of the anticancer drug is only one time in one cycle administration for all the malignant cells. If one cycle of the malignant cells is expressed as a circle; six equally divided points on the circumference of the circle are expressed as administration timings; the circle and points are made a first circle (which corresponds to setting the administration time of the present embodiment); a second circle that has the same size as the first circle is provided; ⅙ of the circumference of the second circle is shown as the G1 phase; the second circle is superposed on the first circuit; and the second circle is rotated on the first circle (which corresponds to various malignant cells advancing the cell cycle in an arbitrary cycle), it is found that the second circle includes only one administration among the six-time administrations of the first circle. In other words, if the basic unit of the divided period is made equal to the period of the G1 phase, in the one cycle administration, the G1 phase corresponds to the administration timing only one time with respect to all of the malignant cells. Hence, it is possible to administer the inhibitor drug at the G1 phase uniformly to all of the malignant cells.

On the other hand, if the divided period of the respective groups is set shorter than the G1 phase, since the G1 phase of the malignant cells may include twice administrations at the beginning and the end of the G1 phase, even in the administration for one cycle, some malignant cells will receive twice administrations of the anticancer drug while other malignant cells will receive one-time administration of the anticancer drug, which may not be a completely averaged administration.

Furthermore, if the divided period is made longer than the period of the G1 phase, because there may be malignant cells whose G1 phase is included in an interval between the administrations, the malignant cells that are not administered in the G1 phase may occur.

In addition, in the administration method of the first embodiment, if the administration period has a certain amount of duration, there may be malignant cells that receive one-time administration of the anticancer drug in the G1 phase and malignant cells that receive double administrations of the anticancer drug in the G1 phase. However, in the event that the divided period is the same as the G1 phase, even if the administration of the G1 phase spans across the two groups, the total anticancer administered time length in a cycle equals among all of the malignant cells, and the anticancer drug can be administered to all the malignant cells in a uniform dosage even in this case.

Therefore, it is possible to make the basic unit for division slightly shorter or longer than the period of G1 phase, which is still expected to be able to obtain a more sufficient effect than the conventional administration method. However, in order to perform a more effective and uniform administration of the anticancer drug, it is preferable to divide the cell cycle by a duration time of a predetermined phase where the anticancer drug acts most effectively as a basic unit, and to set plural groups.

As described above, in the administration apparatus, operating method thereof and administration method of the present embodiment, specified administration apparatus, operating method thereof and administration method are realized by basing on such a view of administering the anticancer drug on the basis of the predetermined period of the cell cycle.

Figure 7:
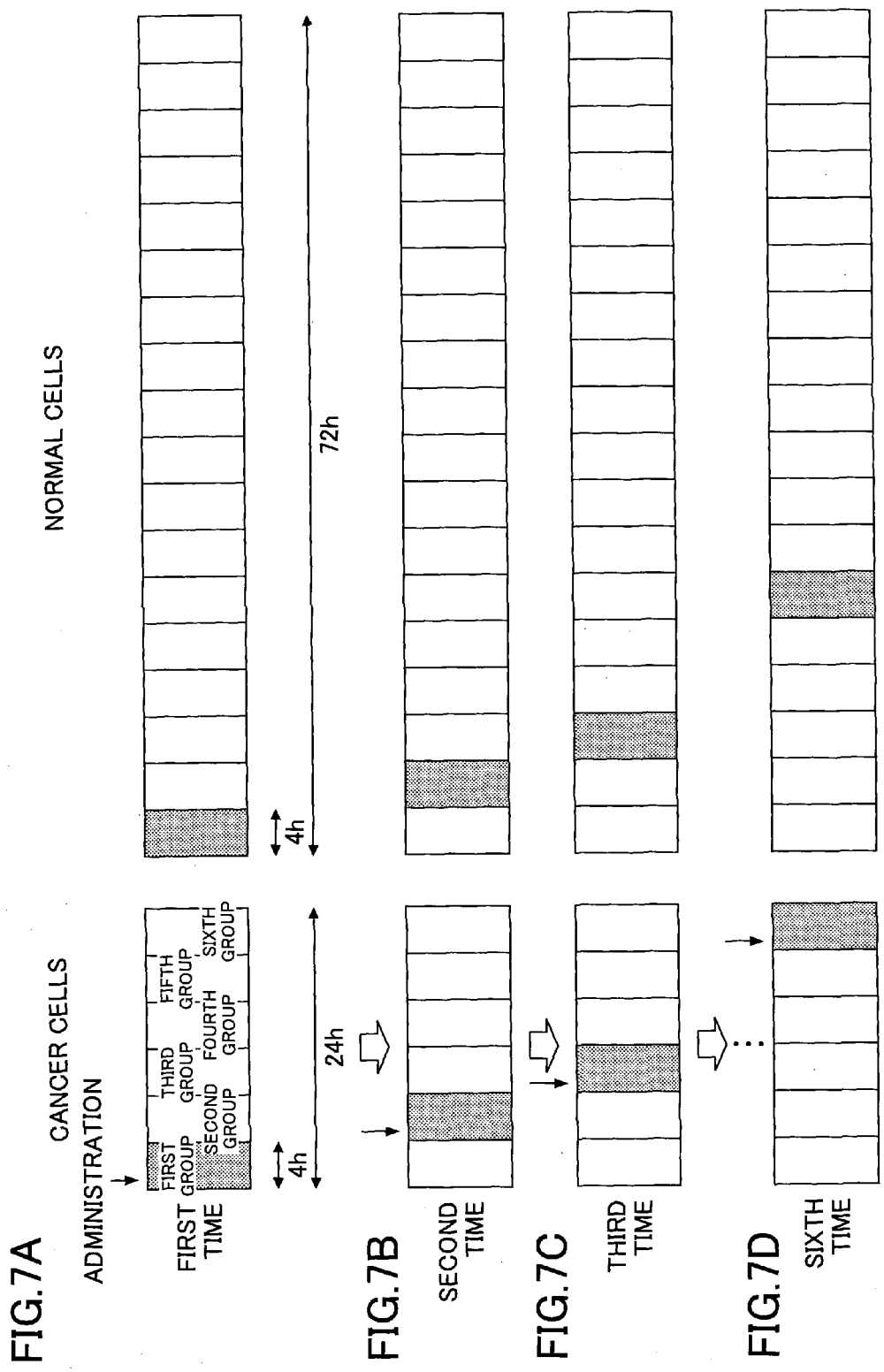
FIG. 7A is a diagram showing an example of a first administration of an administration method of a first embodiment.
FIG. 7B is a diagram showing an example of a second administration of the administration method of the first embodiment.
FIG. 7C is a diagram showing an example of a third administration of the administration method of the first embodiment.
FIG. 7D is a diagram showing an example of a sixth administration of the administration method of the first embodiment.

Here, in FIG. 7, the G1 phase is described to be a phase where the anticancer drug acts effectively. However, since another phase of the cell cycle can be a phase where the anticancer drug works effectively, depending on a combination between the cells and the drug, in that case, another phase of the cell cycle may be a standard.

Hereinafter, a more detailed description is given about specific configuration examples of the administration apparatus, operating method thereof and administration method of the present embodiment. Heretofore, an example of the malignant cell to be necrotized being the cancer cell, and the drug to be used being the anticancer drug is cited. However, because the administration apparatus, operating method thereof and administration method of the present invention can be used for a general malignant cell or tumor that performs cell division, the drug can be generalized and called an inhibitor drug or an inhibitor.

Figure 8:
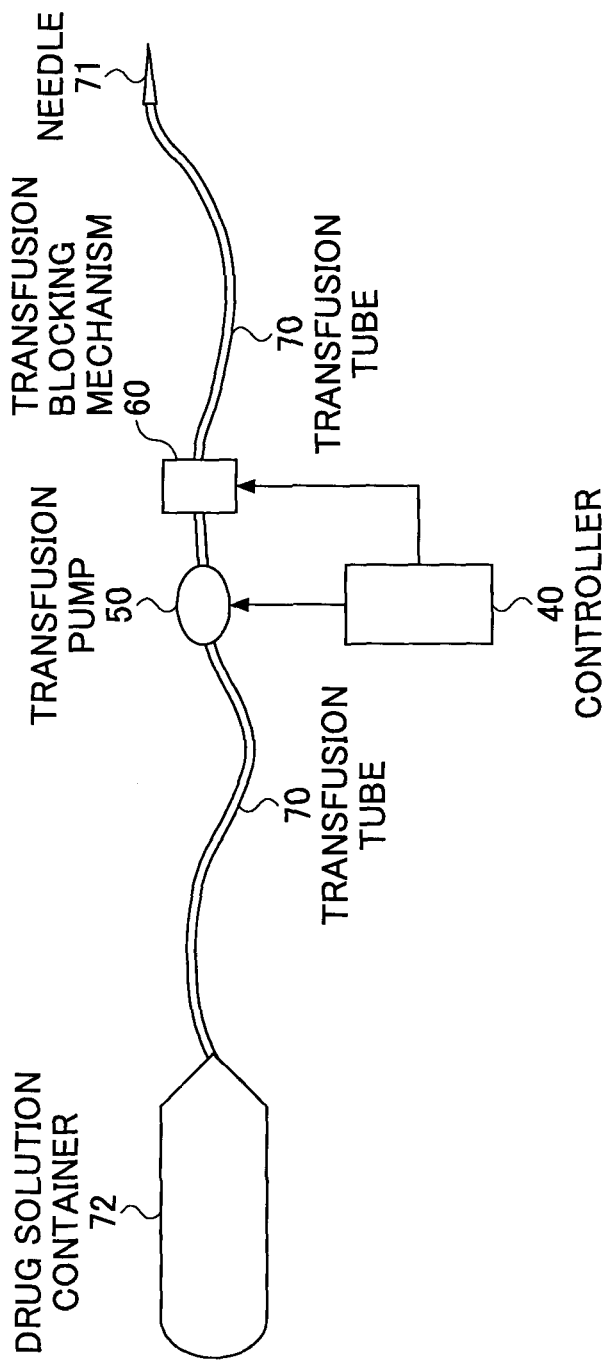
FIG. 8 is a diagram showing an example of a configuration of an administration apparatus of the first embodiment.

FIG. 8 is a diagram showing a configuration of an example of an administration apparatus of a first embodiment of the present invention. In FIG. 8, the administration apparatus of the first embodiment includes a controller 40, a transfusion pump 50, a transfusion blocking mechanism 60, a transfusion tube 70, a needle 71, and a drug solution container (which may be called a drug solution bag) 72. The needle 71 is provided at an end of the transfusion tube 70, and the transfusion pump 50 and the transfusion blocking mechanism 60 are provided in the middle of the drug solution tube 70. The controller 40 is electrically connected to the transfusion pump 50 and the transfusion blocking mechanism 60. For example, the transfusion pump 50, transfusion tube 70, needle 71 and drug solution container 72 may be provided as a transfusion set of a set of assembly.

The administration apparatus of the present embodiment is explained as an administration unit that administers an inhibitor drug into a patient's body, by citing a unit that uses the transfusion pump 50 as an example. If the administration to the patient is performed by using the transfusion pump 50, a drug solution of liquid is used as a drug, and the administration is performed by administering the drug solution into a vein in the patient's body by transfusion. The principle of the administration method of the first embodiment described in FIG. 7 can be applied to general inhibitor drugs that inhibit cell division of malignant cells without limiting the drug solution, and various administration units appropriate for the administrated inhibitor drug can be used. However, to make the explanation easy, the description is given about the administration apparatus using the transfusion hereinafter. However, the administration apparatus, operating method thereof and administration method of the present invention can be applied to various cases of administrating the inhibitor drug that inhibits the cell division of the malignant cells to the patient, and can be used for other intramuscular administration, subcutaneous administration, dermal administration, transnasal administration, parenteral administration such as lung administration, or oral administration and the like. Therefore, the administration apparatus, the operating method thereof and the administration method are not limited to those by transfusion.

The transfusion pump 50 is a transfusion unit to transport the inhibitor drug (i.e., drug solution) contained in the drug solution container 72 through the transfusion tube 70 in a direction toward the needle 71 at the end. Various transfusion pumps 50 are available, as long as the transfusion pump 50 can transport the drug solution.

The transfusion blocking mechanism 60 is a unit to block the transfusion when the drug solution is not administered. The transfusion blocking mechanism 60 may be, for example, a mechanism that clogs a flow channel and blocks the transfusion by pressing the transfusion tube 70 and by compressing the transfusion tube 70 from the outside. In this case, with regard to the method of compressing the transfusion tube 70, for example, a method of compressing the transfusion tube 70 directly by mobile arm driven by a motor, a compressing method by screw and the like can be used according to intended purpose.

The controller 40 is provided as a unit that controls the drive of the transfusion pump 50 and the drive of the transfusion blocking mechanism 60.

Figure 9:
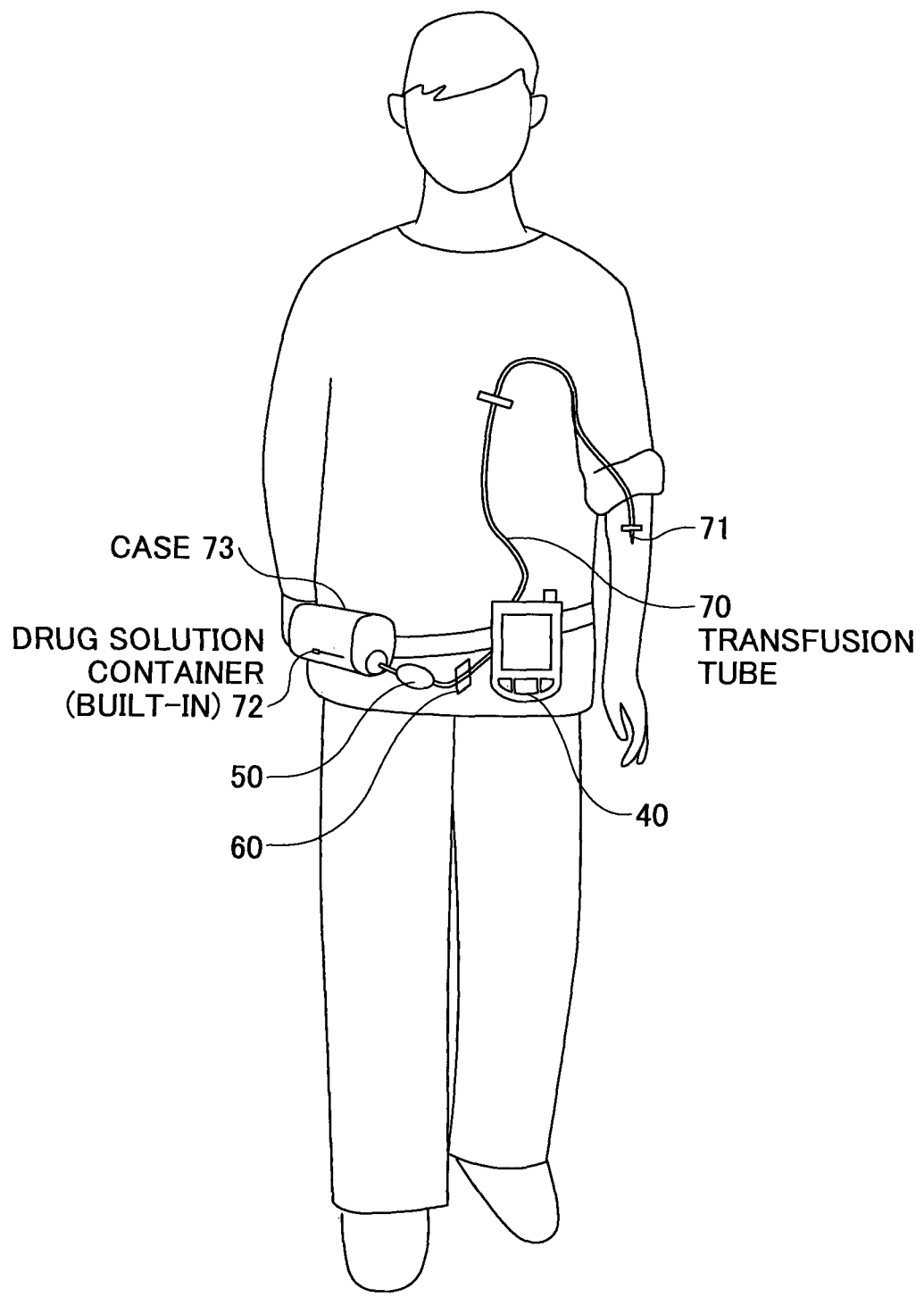
FIG. 9 is a diagram showing an example of a state of having a patient wear the administration apparatus of the first embodiment.

FIG. 9 is a diagram showing an example of a state of having a patient wear the administration apparatus of the first embodiment. The controller 40 is worn around the body of patient. Moreover, the drug solution container 72 that is not shown in FIG. 9 is built into a case 73. The transfusion pump 50 is provided near the case 73 and connected to the drug solution container 72 by the transfusion tube 70, and they are worn around the patient's body in an integrated manner. The transfusion blocking mechanism 60 is worn close to the body of patient as well as the transfusion pump 50. The inhibitor drug transported by the transfusion pump 50 is pumped into the patient's body through the transfusion tube 70 and the needle 71.

Figure 10:
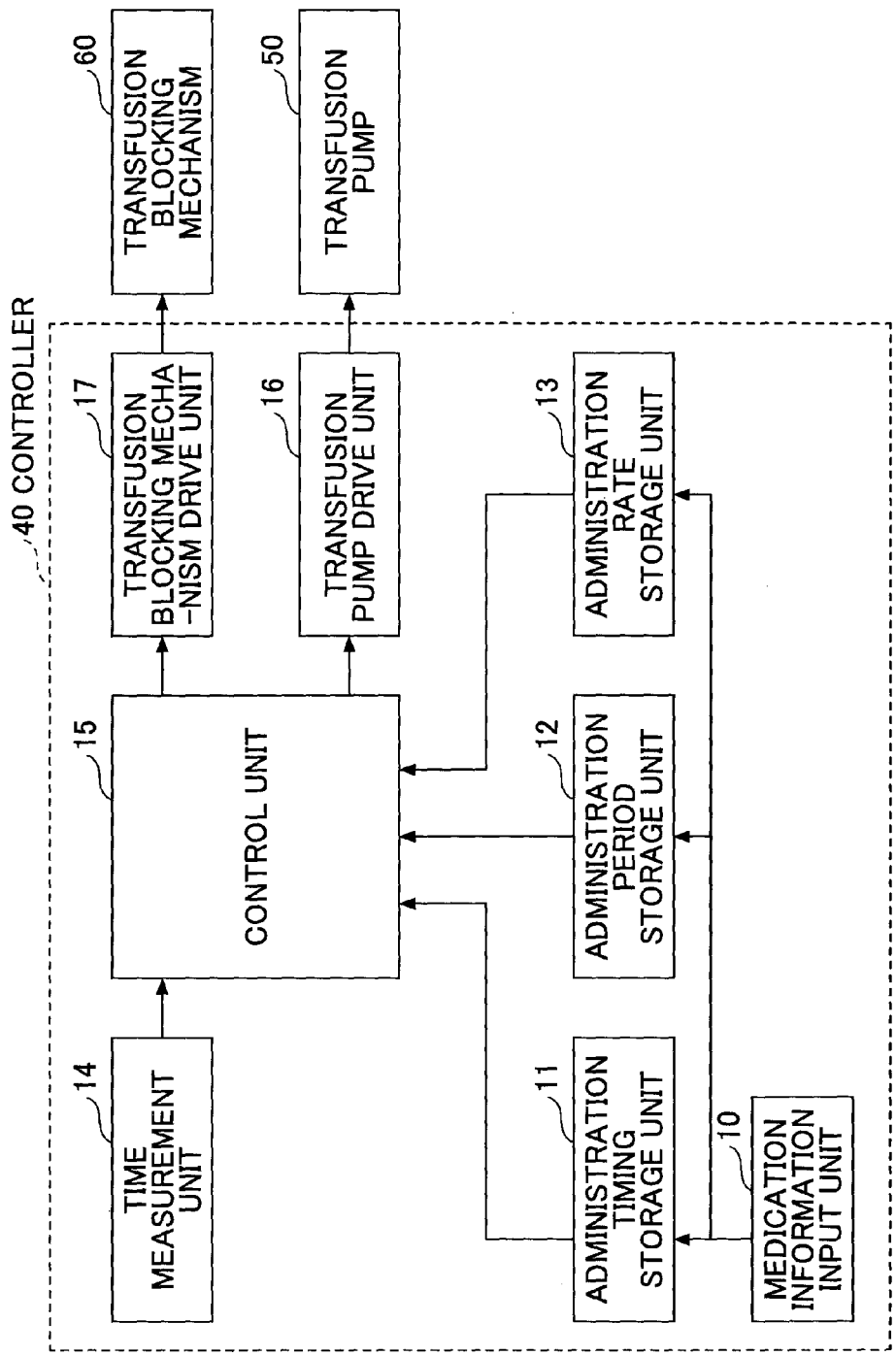
FIG. 10 is a diagram showing an internal configuration of an example of a controller of the administration apparatus of the first embodiment.

FIG. 10 is a diagram showing an example of an internal configuration of the controller 40 of the first embodiment. In FIG. 10, the controller 40 of the first embodiment includes a medication information input unit 10, an administration timing storage unit 11, an administration period storage unit 12, an administration rate storage unit 13, an time measurement unit 14, a control unit 15, a transfusion pump drive unit 16, and a transfusion blocking mechanism drive unit 17. Moreover, in FIG. 10, a transfusion pump 50 and a transfusion blocking mechanism 60 connected to the controller 40 are shown as outside components. The medication information input unit 10 is an input unit to allow a healthcare professional to set an administration timing of the inhibitor drug (e.g., time to start the administration such as at what time?; i.e., what o'clock and minutes), a duration time of the administration and, an administration rate (e.g., as measured in ml per hour). In other words, the controller 40 is configured so that the healthcare professional can set an injecting time interval and an injection dose of the inhibitor drug, that is, a transfusion period and a transfusion rate, depending on the type of inhibitor drug.

Here, the medication information input unit 10 may be configured to allow the healthcare professional to input other related information such as a type of the inhibitor drug and a dosage, and the input information may be determined depending on the intended use. The medication information input unit 10 may be configured to be a selection-type input device such as a touch panel, or may be configured to be an input device into which a setting number is directly input, item by item. The medication information input unit 10 can adopt various configurations and input methods depending on the intended use.

The administration timing storage unit 11 is a unit to store an administration time to start the administration input that is input and set at the medication information input unit 10. Similarly, the administration period storage unit 12 is a unit to store the administration period that is input and set at the medication information input unit 10, and the administration rate storage unit 13 is a unit to store the administration rate that is input and set at the medication information input unit 10. The administration timing storage unit 11, the administration period storage unit 12 and the administration rate storage unit 13 may be configured, for example, to be a rewritable nonvolatile memory such as a flash memory and the like.

The time measurement unit 14 is a unit to measure a current time, and a general timer and the like may be used. In the administration apparatus of the present embodiment, because the set administration time is stored in the administration storage unit 11, whether the current time becomes the administration time can be determined depending on whether the time output from the time measurement unit 14 coincides with the administration time stored in the administration storage unit 11.

The transfusion pump drive unit 16 is a unit to drive the transfusion pump 50. The transfusion pump drive unit 16 may be connected to the transfusion pump 50 and the control unit 15, and may be configured to drive the transfusion pump 50, according to an instruction of the control unit 15.

The transfusion blocking mechanism drive unit 17 is a drive unit to drive or stop the transfusion blocking mechanism 60 according to the instruction from the control unit 15, and is connected to the control unit 15 and the transfusion blocking unit 17. More specifically, the transfusion blocking mechanism drive unit 17 turns the transfusion blocking mechanism 60 off when the transfusion is performed, and turns the transfusion blocking mechanism 60 on when the transfusion is not performed, according to the instruction of the control unit 15. This makes it possible to certainly stop the drug solution provision when the drug solution is not administered.

The control unit 15 is a unit to control the transfusion pump drive unit 16 and the transfusion blocking mechanism drive unit 17, and to administer or not to administer the drug solution at a predetermined timing. The control unit 15 is connected to the transfusion pump drive unit 16 and the transfusion blocking mechanism drive unit 17, and drives the transfusion pump 50 and the transfusion blocking mechanism 60 based on the information stored in the administration timing storage unit 11, the administration period storage unit 12 and the administration rate storage unit 13.

More specifically, the time measurement unit 14 is connected to the control unit 15, and when the time set in the administration timing storage unit 11 and the time output from the time measurement unit 14 coincide, the control unit 15 makes the transfusion blocking mechanism drive unit 17 release the transfusion blocking mechanism 60, and makes the transfusion pump 50 start its operation. After that, the control unit 15 makes the transfusion pump 50 carry out the transfusion at the transfusion rate stored in the administration rate storage unit 13, only for the predetermined period stored in the administration period storage unit 12. After the time elapses the predetermined period, the control unit 15 makes the transfusion pump 50 stop the transfusion, and makes the transfusion blocking mechanism 60 active.

Moreover, the control unit 15 makes the transfusion blocking mechanism drive unit 17 work if the control unit 15 does not make the transfusion pump 50 work, and performs the control to surely stop the administration of the drug solution. In other words, the release of the transfusion blocking mechanism drive unit 17 is performed in accordance with the timing when the transfusion is carried out, and the transfusion is blocked again at the timing of the end of the transfusion by the control unit 15.

In this way, in the administration apparatus of the present embodiment, the transfusion is blocked while the transfusion is not performed by the transfusion blocking mechanism 60 and the transfusion blocking mechanism drive unit 17. By doing this, it is possible to administer the inhibitor drug at a predetermined time interval at exact intervals, and intermittently, and to block the transfusion while the administration is not performed.

Here, the control unit 15, for example, may be configured to be a micro computer that includes a CPU and works by reading a program, or to be an electrical circuit that includes a predetermined operational circuit.

With this configuration, the administration apparatus, operating method thereof and administration method of the first embodiment, as described in FIG. 7, can practice the administration of the inhibitor drug at the timing when the inhibitor drug acts effectively on all of the malignant cells that advance the cell cycle at different timings, though the administration is intermittent. This allows a single administration period to be short, which can reduce the adverse effect on the normal cells, and makes it possible to administer the inhibitor drug to all of the malignant cells in full at the timing when the inhibitor drug exerts effectively on the overall malignant cells such as a malignant tumor and the like.

More specifically, if the administration apparatuses shown in FIGS. 8 through 10 are operated, and the administration method shown in FIG. 7 is practiced, a description is given as follows. Here, as preconditions, as shown in FIG. 7, for a malignant cell that has a 24-hour cell cycle and a 4-hour G1 phase, the 24-hour cell cycle is divided into 4-hour parts, and six groups are set.

If a healthcare professional sets and inputs a first administration time at 0:00 on day X, a second administration time at 4:00 on day (X+1) of 28 hours after the first administration time, a third administration time at 8:00 on day (X+2) of 28 hours after the second administration time, a fourth administration time at 12:00 on day (X+3) of 28 hours after the third administration time, a fifth administration time at 16:00 on day (X+4) of 28 hours after the third administration time, and a sixth administration time at 20:00 on day (X+5) of 28 hours after the third administration time into the medication information input unit 10, the administration times of respective times are set and stored in the administration timing storage unit 11. Also, if the healthcare professional sets an administration period at a predetermined period (for example, P hours) and inputs the predetermined period into the medication information input unit 10 at the same time, a duration time of the respective administration is set at P hours, and the administration period is set and stored to be P hours in the administration period storage unit 12. Similarly, if the healthcare professional sets an administration rate at Q ml/h and inputs the administration rate into the medication information input unit 10, the administration rate is set and stored to be Q ml/h in the administration rate storage unit 13.

In this manner, in a state of setting the administration time in the administration timing storage unit 11, the administration period in the administration period storage unit 12, and the administration rate in the administration rate storage unit 13, the administration starts. Then, each time the current time output from the time measurement unit 14 coincides with the six administration times set in the administration timing storage unit 11 at 28-hour intervals, the control unit 15 releases the drive of the transfusion blocking mechanism drive unit 17, drives transfusion pump drive unit 16, and administers the inhibitor drug to a patient by releasing a blocking state of the transfusion blocking mechanism 60 and by driving the transfusion pump 50. At this time, the administration rate follows the Q ml/h set and stored in the administration rate storage unit 13, and with regard to the administration period, the administration is continuously performed for P hours that have been set and stored in the administration period storage unit 12. After finishing the P-hour continuous administration, the control unit 15 controls the transfusion pump drive unit 16 so as to stop the transfusion pump 50, and controls the transfusion blocking mechanism drive unit 17 so as to drive the transfusion blocking mechanism 60.

By making the controller 40 execute such a control, the administration apparatus of the present embodiment carries out the administration of the inhibitor drug to the patient in an administration pattern shown in FIG. 7, by which the effect on the normal cells can be reduced, and the inhibitor drug is administered to all of the malignant cells at the G1 phase where the administration is effective.

Figure 11:
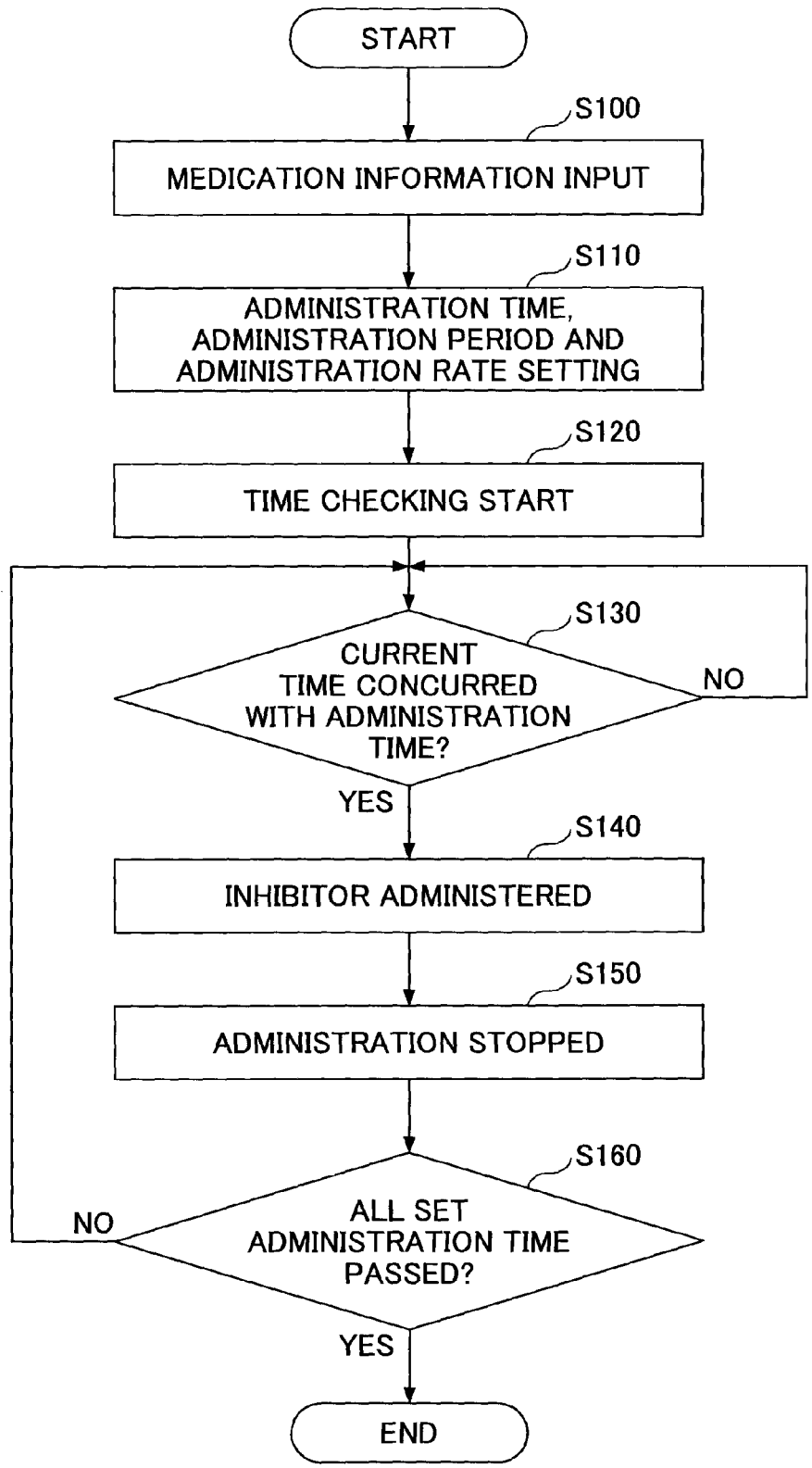
FIG. 11 is an example of a processing flow of an operating method of an administration apparatus and an administration method using the administration apparatus of the first embodiment.

FIG. 11 is a diagram showing an example of an operating method of the administration apparatus and an administration method using the administration apparatus of the first embodiment. In FIG. 11, the same numerals are used for the components similar to those described hereinbefore, and the description is omitted.

In FIG. 11, in step S100, the medication information is input. A healthcare professional may input the medication information including an administration time, an administration period, and an administration rate into the medication information input unit 10.

At that time, the administration time is set on a basis of a predetermined phase of a cell cycle of the target malignant cells to inhibit the cell division thereof. In the example described in FIGS. 6 and 7, the administration time is set on the basis of the G1 phase. In other words, the timing when the inhibitor drug is administered to the malignant cells in the G1 phase is set. If some target malignant cells to be necrotized by inhibiting the cell division can be specified, an inhibitor drug may be administered individually at timing when the phase of the cell cycle of the target malignant cells becomes the G1 phase. However, in general, since the malignant cells exist at a level where the number and respective cell cycles cannot be specified, and the cell cycles of the respective malignant cells advance in different timings, it is difficult to administer the inhibitor drug individually in the G1 phase to all of the malignant cells. Therefore, an administration pattern having administration timing so as to administer all of the malignant cells in the G1 phase without recognizing the cell cycles of the malignant cells individually is established.

As an example, as described in FIG. 7, plural groups are set by dividing the cell cycle by the same period as the duration time of the G1 phase, and the administration time and the administration period are set so as to administer the inhibitor drug to each group among the plural groups in sequence at predetermined intervals. With respect to the administration rate, if there is a value such as default depending on the inhibitor drug type, the default value may be adopted and set.

Here, in FIGS. 6 and 7, a description is given by citing the example of the G1 phase being effective as a period of administering the inhibitor drug, but another period may be timing when the inhibitor drug acts effectively depending on the patient's disease and a used inhibitor drug. In such a case, the administration timing may be determined on a basis of a period when an inhibition effect on cell division by the inhibitor drug functions most effectively.

In step S110, among the medication information input into the medication information input unit 10 by the healthcare professional, the administration time, the administration period and the administration rate are respectively stored in the administration timing storage unit 11, the administration period storage unit 12 and the administration rate storage unit 13, and the administration time, administration period and administration rate are set as information that the control unit 15 refers to.

In step S120, checking the current time with the set administration time is started. Measurement of the current time is performed by the time measurement unit 14. The control unit 15 starts checking and comparison between the current time input from the time measurement unit 14 and the administration time stored in the administration storage unit 11.

In step S130, it is determined whether the current time coincides with the administration time set in the administration timing storage unit 11. The determination is performed by the control unit 15 into which the output from the time measurement unit 14 is input and capable of referring to the administration time stored in the administration timing storage unit 11.

In step S130, if the control unit 15 determines that the current time coincides with the set administration time, the flow advances to step S140. On the other hand, if the control unit 15 determines that the current time does not coincide with the set administration time, the flow enters a stand by state circulating step S130.

In step S140, if the current time is determined to coincide with the administration time in step S130, the administration of the inhibitor drug to the patient is carried out. The administration of the inhibitor drug is performed according to the administration rate and the administration time previously set in steps S100 and S110. With this, the inhibitor drug can be administered at the effective timing to administer the inhibitor drug, and the effect of inhibiting the cell division can be enhanced.

In step S150, after starting the administration, if the administration reaches the set predetermined administration period, the administration is stopped. This allows the inhibitor drug to be administered to the patient only in the predetermined amount in a single administration, which makes it possible to inhibit an adverse effect on the normal cells, and to administer the inhibitor drug effectively.

In step S160, the control unit 15 determines whether the current time goes by all of the administration times set in the administration timing storage unit 11. If the current time has already elapsed the set administration time, this means that all the set administrations have been finished, so the processing flow in FIG. 11 is finished. On the other hand, if the administration time that has not been passed is still set in the administration timing storage unit 11, the flow returns to step S130, enters a standby state that determines whether the current time coincides with the administration time, and enters a state of waiting for the current time passing the remaining administration time.

Figure 13:
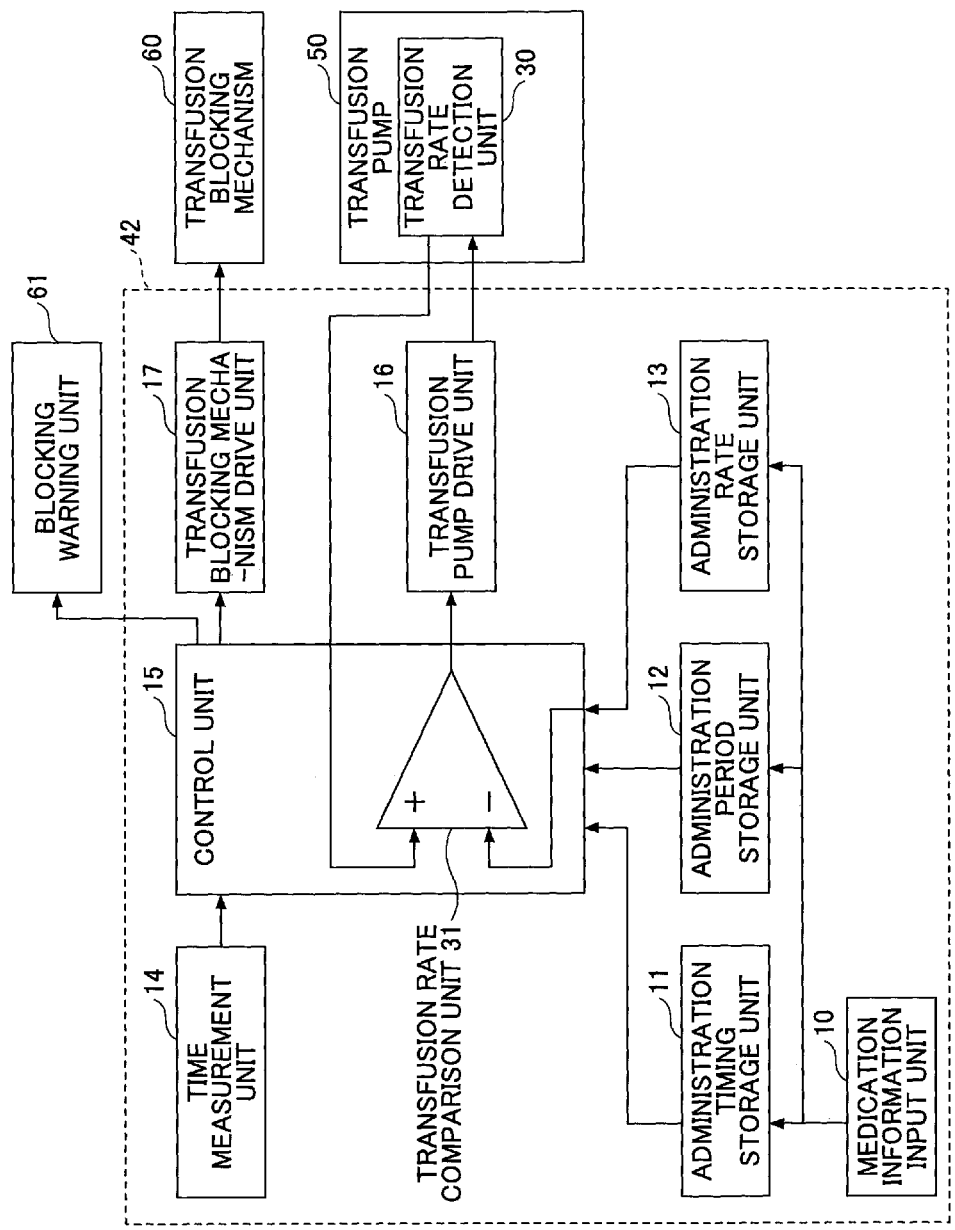
FIG. 13 is a diagram showing an example of a configuration of an administration apparatus of a third embodiment.

Then, in the end, if the inhibitor drug is administrated at all of the set administration time, the flow in FIG. 13 is finished.

Here, in the administration apparatus in the first embodiment, it is also possible to set the transfusion timing, changing the transfusion time intervals depending on the patient's conditions, different from the regular administration setting shown in FIG. 7, by setting and storing arbitrary plural times of information in the administration timing storage unit 11. For example, if a first administration time is made at 0:00 of Y day; a second administration time is made at 2:00 of (Y+1) day; and a third administration time is made at 6:00 of (Y+2) day, a time interval between the first and second administration and a time interval between the second and third administration can be individually set. Besides, elapsed time from the first administration may be directly set such as the second administration being 26 hours later and the third administration being 28 hours later. Also, values set in the administration time storage unit 12 and the administration rate storage unit 14 can be individually set depending on the number of the transfusion (administration). This means that varying the first drug solution amount and the second drug solution amount is possible.

In this manner, according to the administration apparatus, operating method thereof and administration method of the first embodiment, an inhibitor drug can be administered to malignant cells in a predetermined phase in a cell cycle at timing when cell division inhibition effectiveness of the inhibitor drug can acts most efficiently, and only the exact necessary amount of inhibitor drug can be administered corresponding to the cell cycle of the target cells. If such an administration method of the inhibitor drug of the cell division is possible, because the inhibitor drug is not needed to be administered with much for long time as the conventional administration method, the physical strain of the patient can be reduced, and an effective treatment can be performed. Also, the patient does not need to go to a restroom frequently.

Moreover, by performing infusion of the inhibitor drug intermittently plural times, the administration of inhibitor drug of the cell division can be carried out most effectively corresponding to the cell cycle of the target cells. If the explanation is given in the example shown in FIG. 7, by performing the second administration 24 hours+4 hours=28 hours after the first administration, providing the effect for another group of cancer cells is possible. After that, it is possible to repeat the administration every 28 hours, or to change the time intervals depending on the patient's conditions and hospital visit schedule. In short, it is possible to administer the anticancer drug most efficiently and effectively, considering a time ratio between the cell cycle of the cancer cells and a period that the anticancer drug can act effectively, and to reduce strains of both of the patient and healthcare professional.

Second Embodiment

Figure 12:
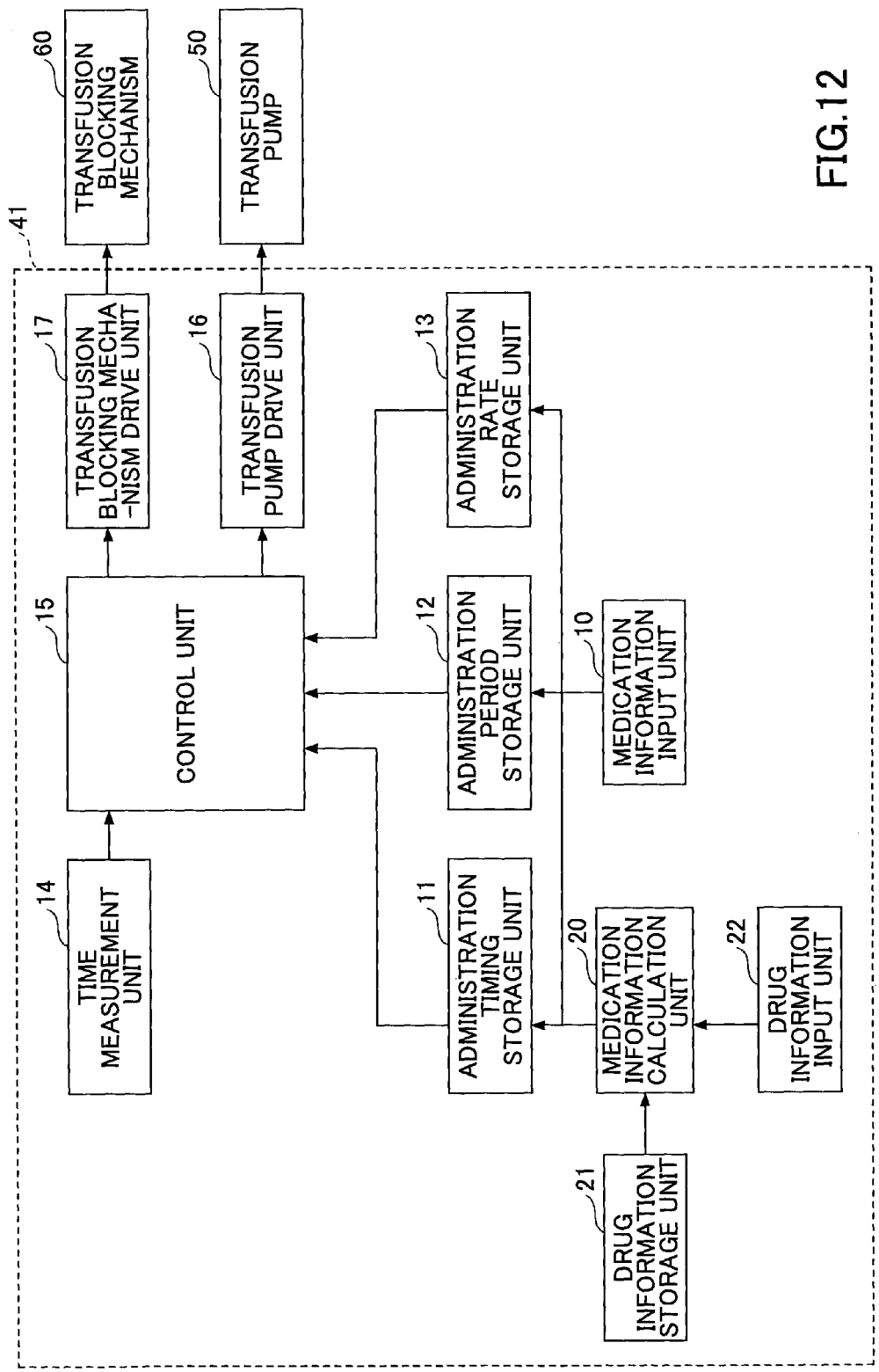
FIG. 12 is a diagram showing an example of a configuration of an administration apparatus of a second embodiment.

FIG. 12 is a diagram showing a configuration of an example of an administration apparatus of a second embodiment of the present invention. The administration apparatus of the second embodiment is similar to the configuration of the administration apparatus of the first embodiment in that a controller 41 includes a medication information input unit 10, an administration timing storage unit 11, an administration time storage unit 13, a time measurement unit 14, a control unit 15, a transfusion pump drive unit 16, and a transfusion blocking mechanism drive unit 17, and further include a transfusion pump 50 and a transfusion blocking mechanism 60. The same numerals are put to components similar to the components described in the first embodiment, and the explanation is omitted.

On the other hand, the administration apparatus of the second embodiment differs in that the controller 40 further include a drug information input unit 20, a drug information storage unit 21 and a medication information calculation unit 22 inside.

The drug information input unit 20 is an input unit that allows a healthcare professional to input drug information to be administered. The drug information input unit 20 is, for example, configured to be sufficient to work if only information to specify the drug such as a type of drug and the like is input.

The drug information storage unit 21 is a database that stores optimum administration information such as administration timing, a dosage and the like for each drug. If the drug is a type of drug that is administered by transfusion, the drug information storage unit 21 stores drug solution information such as transfusion timing, a transfusion amount and the like.

The transfusion information calculation unit 22 is a unit that refers to the drug information stored in the drug information storage unit 21 based on the drug information input into the drug information input unit 20, calculates an optimum administration information for the input drug, and sets respective administration information of the administration time, administration period and administration rate in the administration timing storage unit 11, administration period storage unit 12 and administration rate storage unit 13. This allows the healthcare professional to not need to search and set the optimum drug administration conditions individually, to automatically set a specific operating method of the administration apparatus and administration method by only inputting the information to specify the drug such as type of the drug and the like into the drug information input unit 20, and to reduce his or her strain.

Here, if the optimum administration amount is determined by the drug type, by determining the administration time, administration period and administration rate, when a continuous pair of the administration and non-administration is made a basic cycle, the whole cycle number needed to administer the optimum administration amount is determined. This means that the entire schedule such as period necessary for the whole administration, and the strain of the healthcare professional can be substantially reduced.

Here, the administration apparatus of the second embodiment also includes the medication information input unit 10. In other words, the administration apparatus of the second embodiment is configured to be able to change the administration timing, administration amount, administration rate and the like, by using the medication information input unit 10. This allows the healthcare professional to set a part of the medication information manually and the medication information calculation unit 22 and the like to set the remaining item automatically. For example, it is possible to adopt a using method of setting the administration rate and administration period by the medication information calculation unit 22, and setting only the administration timing by manual using the medication information input unit 10.

Thus, according to the administration apparatus, operating method thereof and administration method, time intervals that administer the inhibitor drug, an amount of the inhibitor drug to be administered, a type of the inhibitor drug, and the other settings related to the administration of the inhibitor drug are automatically practiced by being preliminarily set. Because of this, even if the administration time is midnight, the healthcare professional such as a doctor or a nurse do not need to bear a burden with respect to the administration directly. In addition, for a patient, a hospital admission is not a necessary condition for a treatment, because the inhibitor drug is automatically administered at necessary timing for the treatment for 24 hours. Moreover, in the case of hospital admission, if the administration time comes in midnight, since the administration is performed automatically, the patient can receive the administration in a stable state. Furthermore, because the treatment can be continued in home healthcare, the patient can be released from the economic stress and the stress of hospitalization.

In this way, according to the administration apparatus, operating method thereof and administration method, by increasing a degree of automatic setting of the administration setting, the strain of the healthcare professional and the patient can be substantially reduced, and the administration of the inhibitor drug can be performed effectively, reducing the adverse effect on the normal cells.

Third Embodiment

FIG. 13 is a diagram showing a configuration of an example of an administration apparatus of a third embodiment of the present invention. In FIG. 13, the administration apparatus of the third embodiment is common to the administration apparatus of the first embodiment in that the administration apparatus includes a medication information input unit 10, an administration timing storage unit 11, an administration period storage unit 12, an administration rate storage unit 13, a time measurement unit 14, a control unit 15, a transfusion pump drive unit 16, and a transfusion blocking mechanism drive unit 17 inside the controller 42, and a transfusion pump 50 and a transfusion blocking mechanism 60 outside the controller 42. Here, the same numerals are used for components similar to those in the first embodiment, and the description is omitted.

In the meanwhile, the administration apparatus of the third embodiment differs from the administration apparatus of the first embodiment in that a transfusion rate comparison unit 31 is provided inside a control unit 15 in the controller 42, and a transfusion rate detection unit 30 is provided inside the transfusion pump 50. Also, the administration apparatus of the third embodiment may include a blocking warning unit 61 outside the controller 42.

The transfusion rate detection unit 30 is a unit to detect a transfusion rate in the transfusion pump 50 or the transfusion tube 70. For example, a flow sensor and the like may be used for the transfusion rate detection unit 30. The transfusion rate detection unit 30 is provided inside the transfusion pump 50 or in the neighboring transfusion tube 70. FIG. 13 shows an example of providing the transfusion rate detection unit 30 inside the transfusion pump 50.

The transfusion rate comparison unit 31 is a unit that compares an actual transfusion rate inside the transfusion pump 50 or the neighboring transfusion tube 70 with an administration rate (i.e., transfusion rate) set in the administration rate storage unit 13. For example, a comparator and the like may be used for the transfusion rate comparison unit 31.

The blocking warning unit 61 is a unit to warn outward that the channel for the drug solution is blocked if the actual transfusion rate is over a predetermined standard transfusion rate.

In FIG. 13, an output of the transfusion rate detection unit 30 is compared with an output of the administration rate storage unit 13 by the transfusion rate comparison unit 31, and the control unit 15 controls the transfusion pump drive unit 16 based on the comparison result. With this, a feedback control is performed so that the amount of drug injected into the patient's body per unit time constantly agrees with the value set in the administration rate storage unit 13.

In this manner, in the administration apparatus of the third embodiment, the transfusion rate detection unit 30 detects the actual transfusion rate in real time, and the transfusion rate is controlled by the feedback control based on the detection value. Because of this, since the transfusion rate is controlled so as to be constantly the same as the value set in the administration rate storage unit 13, even if there is disturbance such as a back pressure change from the body, a gravity change due to a height difference between the needle 71 and the drug solution bag 72 and the like, a transfusion of a constant flow rate can be accurately performed by canceling the effect. This makes it possible to realize a stable treatment even if the inhibitor drug has the effect in a very small amount, to put it the other way around, even if the inhibitor drug needs to be strictly managed about the dosage.

Moreover, in the transfusion rate detection unit 30, should the flow rate over the predetermined set value be detected, the transfusion rate comparison unit 31 detects the abnormal transfusion rate. At this time, the control unit 15 immediately controls the transfusion blocking mechanism drive unit 17, and a control that stops the transfusion may be performed. Also, the controller 42 may drive the blocking warning unit 61 so as to warn outside people that the channel for the drug solution is blocked. This makes it possible to safely prevent the flow rate over the regulated amount from being administrated into the body.

Here, the contents described in the first embodiment can be directly applied to the operating method of the administration apparatus and administration method using the same of the third embodiment. Because the transfusion rate can be more accurately managed in the operating method of the administration apparatus and the administration method than those in the first embodiment, the inhibitor drug can be administered more accurately in the third embodiment than the first embodiment.

Fourth Embodiment

FIGS. 14A through 14E are diagrams to illustrate an operating method of an administration apparatus and an administration method of a fourth embodiment of the present invention. The operating method of the administration apparatus and the administration method of the fourth embodiment can be commonly performed in the administration apparatus of the first through third embodiments, the operating method of the administration apparatus and the administration method of the fourth embodiment are described without particularly distinguishing the first through third embodiments.

The administration method described in FIG. 7 in the first embodiment is a method of dividing the 24-hour cell cycle by 4-hour G1 phase into six groups, and administrating the inhibitor drug in sequence at 28-hour intervals for the first through sixth groups.

However, for the first through sixth groups, it is not necessary to administer the inhibitor drug, and it is possible to administer the inhibitor drug every other group. Moreover, it is not necessary to perform administration every cell cycle, but is possible to perform administration at plural cycle intervals such as every two cycle or every three cycles. In the operating method of the administration apparatus and the administration method of the fourth embodiment, a description is given about such an administration method. Here, in FIG. 14, with respect to the cell cycle, administration period and divided group number, similar to FIG. 7, the description is given by citing an example of the cell cycle being made 24 hours, the administration period being made 4 hours, and the divided group number being made six.

FIG. 14A is a diagram showing an example of a first administration of the administration method of the fourth embodiment. In the first administration, an inhibitor drug is administered to the first group.

FIG. 14B is a diagram showing an example of a second administration of the administration method of the fourth embodiment. In FIG. 14B, in the second administration, the inhibitor drug is administered to the third group. At this time, the administration time is 56 hours after the first administration. In other words, from the first administration time, two-cycle interval longer than the one cycle is taken, and by further adding the time intervals of the first group and the second group, the inhibitor drug is administered to the third group.

FIG. 14C is a diagram showing an example of a third administration method of the fourth embodiment. In the third administration, the inhibitor drug is administered to the fifth group. In this case also, a 56-hour interval is taken for the second administration time.

FIG. 14D is a diagram showing an example of a fourth administration of the administration method of the fourth embodiment. In the fourth administration, the inhibitor drug is administered to the second group. A 36-hour interval is taken from the third administration time. The interval is shorter than 48 hours corresponding to a two-cycle period, but longer than 24 hours corresponding to a one-cycle period, so the administration is performed at a sufficient time interval.

FIG. 14E is a diagram showing an example of a sixth administration of the administration method of the fourth embodiment. Here, though a fifth administration is not shown in FIGS. 14E and 14E, the fifth administration is performed to the fourth group by taking a 32-hour interval for the fourth administration, and the sixth administration in FIG. 14E is carried out to the sixth group. In this case also, a 32-hour interval is taken from the fifth administration.

In this manner, it is not always to administer the inhibitor drug to the divided groups in sequence, if the administration intervals are sufficiently taken, the administration is executed in arbitrary order to the divided groups. In addition, the longer the administration intervals, the smaller the effect provided for the normal cells by the administration. Accordingly, the intervals of the plural cycles may be taken longer than the one-cycle period. Though the whole administration requires a long period, since the accumulative administration period is short, considering a patient's sufficient restoration of strength, the inhibitor drug can be administered to each group effectively, without affecting the normal cells in an adverse way. Here, in the fourth embodiment, the administration to the normal cells can be limited to 24/72=1/3.

In addition, in the fourth embodiment, the description is given by citing the example of administering the inhibitor drug to every other group, but the administration may be performed at (nT+t) intervals in the administration method in the first embodiment. Here, "T" is a cell cycle of a malignant cell; "t" is a duration time of a predetermined period of performing the administration; and "n" is a natural number not less than two.

As described in the first embodiment and the fourth embodiment, if the time intervals before and after the administration time is set to have time intervals not less than at least a one-cycle period, intervals such that the normal cells do not receive the effect by the administration can be sufficiently provided between the successive administrations. Moreover, by performing the administration in sequence by making the divided group a target, the administration can be carried out to all the malignant cells in full at timing when the inhibitor drug can act effectively.

Thus, by making an intermittent administration pattern that does not occur a continuous administration for a long period of time, diluting the concentration of the drug solution is not necessary, and performing the administration at an appropriate concentration that has a sufficient effect on inhibition of cell division of the malignant cells is possible. By removing the necessity of diluting the concentration, the whole dosage can be reduced, and the frequency of the urination of the patient can be reduced, which makes it possible to reduce strain on a patient.

Here, as described in the first and fourth embodiment, with respect to the administration order of the inhibitor drug to the plural groups, various orders of the administration patterns can be considered, but the administration pattern such that a difference of the number of administrations among the groups is not more than once may be adopted. By performing such an administration, a simultaneous occurrence of a group to which any inhibitor drug is not administered and a group to which the inhibitor drug is administered not less than twice can be removed. In other words, if there is a group that has received an administration one extra time, the administration to the group can be stopped until the other group receives the same times of administration as the group, the inhibitor drug can be administered so as to be uniform to all of the groups. This administration method can be applied not only to the case of the administration for only a one-cycle period of the cell cycle, but also to the case of the administration for cycles across not less than a two-cycle period. This means that the second-round administrations are not started before the first-round administrations are not performed to all the groups, and the next round administrations can be started after finishing respective round administrations.

Furthermore, the number of administration of the inhibitor drug is preferably set at the number equal to or more than the plural groups, and the not less than once administration is preferably performed, in terms of administering the inhibitor drug to all the malignant cells at the G1 phase at least once.

In this manner, according to the administration method of the fourth embodiment, it is possible to reduce the adverse effect on the normal cells and to inhibit the cell division of the malignant cells effectively, using the various administration patterns.

Fifth Embodiment

FIGS. 15A through 15D are diagrams showing an example of an operating method of an administration apparatus and an administration method of a fifth embodiment of the present invention. FIG. 15A is a diagram showing an example of a first administration of the operating method of the administration apparatus and the administration method of the fifth embodiment. FIG. 15B is a diagram showing an example of a second administration of the operating method of the administration apparatus and the administration method of the fifth embodiment. FIG. 15C is a diagram showing an example of a third administration of the operating method of the administration apparatus and the administration method of the fifth embodiment. FIG. 15D is a diagram showing an example of a sixth administration of the operating method of the administration apparatus and the administration method of the fifth embodiment.

The operating method of the administration apparatus and the administration method of the fifth embodiment differ from the administration method in FIG. 7 of the first embodiment in that a cell cycle of a malignant cell is 22 hours. The operating method of the administration apparatus and the administration method of the fifth embodiment are similar to the administration method in FIG. 7 in that a duration time of the G1 phase of the cell cycle of the malignant cell is four hours and the cell cycle is divided into six groups. The other preconditions are made similar to the administration method in FIG. 7. Here, the cell cycle becomes shortened to 22 hours, by which the number of the malignant cells in the G1 phase in the sixth group is thought to be about a half of the number of the malignant cells in the G1 phase of the other groups. The operating method of the administration apparatus and the administration method of the fifth embodiment differ from the administration method in FIG. 7 of the first embodiment in that the sixth group is made like a fraction to the other groups.

Here, since the operating method of the administration apparatus and the administration method of the fifth embodiment can be practiced in the administration apparatuses of the first through third embodiments, a description is given without particular limitations.

As shown in FIG. 15A, in a first administration, the inhibitor drug is administered to the malignant cells of a first group in the G1 phase at first administration timing as a target. The inhibitor drug, effectively exerts the cell division inhibition effect on the malignant cells in the first group that enter the G1 phase at the first administration timing.

As shown in FIG. 15B, in a second administration, the inhibitor drug is administered to the malignant cells of a second group in the G1 phase at second administration timing as a target, at 26 hours after the first administration time. The inhibitor drug produces the cell division inhibition effect on the malignant cells in the second group that enter the G1 phase at the second administration timing.

As shown in FIG. 15C, in a third administration, the inhibitor drug is administered to the malignant cells of a third group in the G1 phase at third administration timing as a target, at 26 hours after the second administration time. The inhibitor drug effectively exerts the cell division inhibition effect on the malignant cells in the third group that enter the G1 phase at the third administration timing.

After that, similar administrations are repeated as a fourth and a fifth administrations.

As shown in FIG. 15D, in a sixth administration, the inhibitor drug is administered to a sixth group 26 hours after the fifth administration time. Four hours are allotted to the first though sixth groups, but a half of only two hours are allotted to the sixth group. Hence, the number of the malignant cells that enters the G1 phase included in the sixth group is about a half of the number of the malignant cells that enters the G1 phase included in the respective first through fifth groups. In this case, for example, the sixth administration period may be a half of the respective first through fifth administration periods, and the dosage of the inhibitor drug to the malignant cells belonging to the sixth group (i.e., being in the sixth group at the sixth administration timing) may be a half of the dosage to the malignant cells belonging to the respective first through fifth groups. This makes it possible to administer the inhibitor drug to the malignant cells in the first through sixth groups uniformly. Thus, if the cell cycle is divided by a duration time of a predetermined phase where the inhibitor acts effectively, the cell cycle cannot be divided into all equal parts, and a fraction can occur. Even in this case, by regarding the broken number as a single independent group, and for the broken number of group, by setting an administration period (i.e., dosage) corresponding to the group length or the number of the malignant cells included in the group, the administration methods described in the first and the fourth embodiments can be directly applied.

In this case, the effect that the inhibitor drug provide for the normal cells is $22/72=11/36<1/3$, and can be smaller than the case of the first and fourth embodiments.

Here, in the fifth embodiment, the sixth group of the last broken number is treated as the independent group, but by adding the broken number group to the fifth group, the administration period to the fifth group may be lengthened corresponding to the length of the broken number. In this case, the administrations are finished at five times to all of the plural groups of one cell cycle.

In this way, the group division method may base the duration time of the predetermined phase as a basic unit, but if the broken number occurs, by treating the group of the broken number as an individual group and by shortening the administration period to the group, the entire dosage can be adjusted. Or, by adding the group of the broken number to the other group and by lengthening the administration period to the group, the entire dosage can be adjusted. By doing this, an appropriate administration can be performed.

Here, if the intermittent administration of the inhibitor drug is carried out for plural cycles over one cycle of the cell cycle, the broken number may be ignored and the administration of the inhibitor drug may be performed making all the group an equal time length. In the second cycle, though the divided place of the group is different from the first cycle, since the cell cycle is properly divided into plural groups in the respective cycles, by executing the administration on the basis of the group, the administration can be performed so as to reduce the effect on the normal cells, and so as to work the inhibitor drug effectively, similarly to the other embodiments.

According to an administration apparatus, an operating method thereof, and an administration method of one embodiment, cell division of a malignant cell can be effectively inhibited, and an adverse effect on a normal cell can be reduced.

The embodiments of the present invention can be applied to an administration apparatus, an operating method thereof and an administration method that use various administration units such as a transfusion pump and the like.

The present invention is not limited to these embodiments, but variations and modifications may be made without departing from the scope of the present invention.

The present application is based on Japanese Priority Patent Application No. 2010-205881, filed on Sep. 14, 2010, the entire contents of which are incorporated herein by reference.

The invention claimed is:

1. An administration apparatus to administer an inhibitor drug to a patient to inhibit cell division of a malignant cell comprising:
    an administration unit configured to administer the inhibitor drug to the patient;
    an administration timing storage unit configured to store an administration time to start an administration of the inhibitor drug;
    a time measurement unit configured to measure a current time; and
    a control unit configured to drive and control the administration unit so as to administer the inhibitor drug to the patient when the current time coincides with the administration time,
    wherein the administration time is set on a basis of a predetermined phase of a cell cycle of the malignant cell,
    a phase when a cell division inhibition effect by the inhibitor drug is the highest is selected as the predetermined phase in the cell cycle;
    the cell cycle is divided into a plurality of groups by a predetermined period not more than a duration time of the predetermined phase; and
    the administration time is intermittently set plural times at not less than (T+t) intervals if the cell cycle is a duration time T, and the predetermined period is a duration time t, and is set so that a difference of respective sequential administration times for the plurality of groups is less than a two cycle period.

2. The administration apparatus as claimed in claim 1, wherein the predetermined period is set at the duration time of the predetermined phase.

3. The administration apparatus as claimed in claim 2, further comprising:
    an administration period storage unit to store an administration period to administer the inhibitor drug continuously,
    wherein the administration period is set at not more than the duration time of the predetermined phase.

4. The administration apparatus as claimed in claim 3, wherein the administration time is set so that intervals before and after the administration time equal (AT+t) if A is made a constant of a natural number.

5. The administration apparatus as claimed in claim 3, further comprising:
    an administration rate storage unit to store an administration rate to administer the inhibitor drug; and
    a medication information input unit to allow medication information to be input,
    wherein a dosage is input and set through the medication information input unit, and a continuous combination of administration and non-administration of the inhibitor drug is made a basic cycle based on the dosage, the administration time, the administration period, and the administration rate; and
    wherein a whole control including a number of the units needed to administer the dosage to the patient, and the control unit perform the whole control automatically.

6. The administration apparatus as claimed in claim 1, wherein the administration time is set at a number not less than the number of the plural groups.

7. The administration apparatus as claimed in claim 1, wherein the malignant cell is a cancer cell; and
the inhibitor drug is a anticancer drug.

8. The administration apparatus as claimed in claim 1, wherein the inhibitor drug is a drug solution; and
the administration unit administers the drug solution by transfusion to a blood circulating system in the patient's body.

9. The administration apparatus as claimed in claim 8, wherein the administration unit includes a transfusion pump.

10. The administration apparatus as claimed in claim 8, wherein the administration unit includes a blocking unit to block a channel for the transfusion during the non-administration.

11. The administration apparatus as claimed in claim 10, wherein the administration unit includes a flow sensor in the channel for the transfusion, and
the control unit performs a feedback control so as to make a flow rate of the drug solution constant, based on a flow rate value detected by the flow rate sensor.

12. The administration apparatus as claimed in claim 11, further comprising:
    a blocking warning unit to warn that the channel for the drug solution is blocked,
    wherein the control unit blocks the channel for the drug solution by the blocking unit, and warns that the channel for the drug solution is blocked by driving the blocking warning unit if the flow rate value detected by the flow rate sensor is over a predetermined standard value.

13. An operating method of an administration apparatus, the administration apparatus including, an administration unit configured to administer an inhibitor drug to a patient to inhibit cell division of a malignant cell;

an administration timing storage unit configured to store an administration time at which to start an administration of the inhibitor drug;

a time measurement unit configured to measure a current time;

an administration period storage unit to store an administration period of administering the inhibitor drug continuously to the patient; and a control unit configured to drive and control the administration unit so as to administer the inhibitor drug to the patient when the current time coincides with the administration time, the operating method comprising the steps of:

setting the administration time and the administration period on a basis of a predetermined phase of the cell cycle of the malignant cell;

storing the set administration time in the administration time storage unit and the set administration period in the administration period storage unit respectively; and administering the inhibitor drug to the patient continuously for the administration period when the current time measured by the time measurement unit coincides with the administration time by controlling the administration unit with the control unit, wherein a phase when a cell division inhibition effect by the inhibitor drug is the highest is selected as the predetermined phase in the cell cycle;

the cell cycle is divided into a plurality of groups by a predetermined period not more than a duration time of the predetermined phase; and the administration time is intermittently set plural times at not less than (T+t) intervals if the cell cycle is a duration time T, and the predetermined period is a duration time t, and is set so that a difference of respective sequential administration times for the plurality of groups is less than a two cycle period.

14. An administration method to administer an inhibitor drug to a patient to inhibit cell division of a malignant cell, comprising the steps of:

setting an administration time to start an administration of the inhibitor drug to the patient on a basis of a predetermined phase of the cell cycle division of the malignant cell;

storing the set administration time in an administration time storage unit; and administering the inhibitor drug to the patient continuously when the current time coincides with the administration time stored in the administration storage unit, wherein a phase when a cell division inhibition effect by the inhibitor drug is the highest is selected as the predetermined phase in the cell cycle;

the cell cycle is divided into a plurality of groups by a predetermined period not more than a duration time of the predetermined phase; and the administration time is intermittently set plural times at not less than (T+t) intervals if the cell cycle is a duration time T, and the predetermined period is a duration time t, and is set so that a difference of respective sequential administration times for the plurality of groups is less than a two cycle period.

\* \* \* \* \*